United States Patent
Grove et al.

(10) Patent No.: US 8,952,001 B2
(45) Date of Patent: Feb. 10, 2015

(54) AMINO-HETEROARYL DERIVATIVES AS HCN BLOCKERS

(75) Inventors: Simon James Anthony Grove, Newhouse (GB); Angus John Morrison, Wishaw (GB); Craig Jamieson, Newhouse (GB); Ronald Palin, Newhouse (GB); John Kinnaird Ferguson Maclean, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 197 days.

(21) Appl. No.: 13/518,427

(22) PCT Filed: Dec. 20, 2010

(86) PCT No.: PCT/EP2010/070213
§ 371 (c)(1),
(2), (4) Date: Jun. 22, 2012

(87) PCT Pub. No.: WO2011/076723
PCT Pub. Date: Jun. 30, 2011

(65) Prior Publication Data
US 2012/0264728 A1    Oct. 18, 2012

Related U.S. Application Data

(60) Provisional application No. 61/289,182, filed on Dec. 22, 2009.

Foreign Application Priority Data

Dec. 22, 2009    (EP) .................................. 09180321

(51) Int. Cl.
| | | |
|---|---|---|
| *A61K 31/505* | (2006.01) | |
| *A61K 31/506* | (2006.01) | |
| *A61K 31/444* | (2006.01) | |
| *A61K 31/53* | (2006.01) | |
| *A61K 31/4439* | (2006.01) | |
| *A61K 31/4427* | (2006.01) | |
| *C07D 239/42* | (2006.01) | |
| *C07D 401/04* | (2006.01) | |
| *C07D 401/12* | (2006.01) | |
| *C07D 251/42* | (2006.01) | |
| *C07D 403/12* | (2006.01) | |
| *A61K 31/435* | (2006.01) | |
| *A61K 31/497* | (2006.01) | |
| *C07D 213/73* | (2006.01) | |

(52) U.S. Cl.
CPC ............ *C07D 239/42* (2013.01); *A61K 31/435* (2013.01); *A61K 31/497* (2013.01); *A61K 31/506* (2013.01); *A61K 31/53* (2013.01); *C07D 213/73* (2013.01); *C07D 401/12* (2013.01); *C07D 403/12* (2013.01)
USPC ... 514/210.2; 514/275; 514/335; 514/255.05; 514/352; 514/343; 514/245; 544/331; 544/332; 544/295; 544/211; 546/261; 546/268.1; 546/276; 546/311

(58) Field of Classification Search
CPC .. C07D 239/42; C07D 401/04; C07D 401/12; C07D 251/42; C07D 403/12; A61K 31/505; A61K 31/506; A61K 31/444; A61K 31/53; A61K 31/44; A61K 31/4439; A61K 31/4427
USPC ......... 514/210.2, 275, 335, 255.05, 352, 343, 514/245; 544/331, 332, 295, 211; 546/261, 546/268.1, 276, 311
See application file for complete search history.

(56) References Cited

U.S. PATENT DOCUMENTS

2007/0135437 A1* 6/2007 Benjamin et al. ............. 514/241
2008/0055826 A1    3/2008 Smith et al.

FOREIGN PATENT DOCUMENTS

| EP | 0856283 A1 | 5/1998 |
|---|---|---|
| WO | 2006030378 A1 | 3/2006 |
| WO | 2010052198 A1 | 5/2010 |

OTHER PUBLICATIONS

Chaplan, et al., :Neuronal Hyperpolarization—Activated Pacemaker Channels Drive Neuropathic Pain, Journal of Neuroscience, Feb. 2003, vol. 23, No. 4, pp. 1169-1178.
(Continued)

*Primary Examiner* — James O Wilson
*Assistant Examiner* — Ebenezer O Sackey
(74) *Attorney, Agent, or Firm* — H. Eric Fischer; John C. Todaro

(57) ABSTRACT

The invention relates to amino-heteroaryl derivatives having the general Formula I or a pharmaceutically acceptable salt thereof, to pharmaceutical compositions comprising the same, as well as to the use of these derivatives for the treatment of pain, such as neuropathic pain or inflammatory pain.

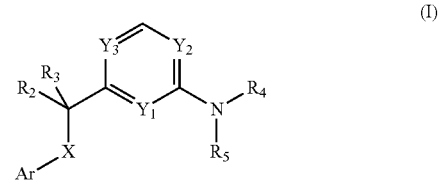

(I)

10 Claims, No Drawings

(56) References Cited

OTHER PUBLICATIONS

Dalle, et al., "Peripheral Block of the Hyperpolarization-Activated Cation Current (Ih) Reduces Mechanical Allodynia in Animal Models of Postoperative and Neuropathic Pain," Regional Anesthesia and Pain Medicines, vol. 30, No. 3, 2005, pp. 243-248.

Wickenden, et al., "HCN Pacemaker Channels and Pain: A Drug Discovery Perspective," Current Pharmaceutical Design, 2009, vol. 15, pp. 2149-2168.

WO10176723 Search Report.

* cited by examiner

AMINO-HETEROARYL DERIVATIVES AS HCN BLOCKERS

CROSS REFERENCE TO RELATED APPLICATIONS

This application is a U.S. National Phase application under 35 U.S.C. §371 of PCT Application No. PCT/EP2010/070213, filed Dec. 20, 2010.

This invention relates to amino-heteroaryl derivatives, to pharmaceutical compositions comprising the same and to the use of these amino-heteroaryl derivatives in the treatment of chronic neuropathic pain.

Neuropathic pain, or the spontaneous pain and abnormal sensitivity following a nerve injury, typically results from a traumatic injury, an infection or disease, or surgery, and can persist long after the initial injury has healed. Current treatment options are limited or inadequate for many people.

HCN channels are the molecular substrates of the currents known as $I_h$, $I_f$ or $I_q$. Hyperpolarization-activated, cyclic nucleotide-gated (HCN) channels, also known as pacemaker channels, first identified in cardiac pacemaker cells (Di Francesco, 1993 Annu Rev Physiol. 55:455-472), have also been found in a variety of peripheral and central neurones (e.g. Notomi & Shigemoto 2004 J. Comp. Neurol. 471: 241-276). These channels are slowly activated by hyperpolarization to generate depolarizing inward current (termed $I_f$ in cardiac cells and $I_h$ in neurones) and are permeable to both sodium and potassium ions. The four HCN channel isoforms are present in pain-processing regions of the nervous system including thalamus, amygdala, spinal cord & primary sensory neurones. It is likely that all four subunits are present in dorsal root ganglia (DRG), with HCN1 having the highest level of expression. This is consistent with the activation kinetics of $I_h$ current recorded from DRG (Tu et al., J Neurosci. Res. 2004 76:713-722).

$I_h$ current has been detected in neurons from many regions of the nervous system involved in nociception, including the substantia gelatinosa of spinal cord, dorsal root ganglia, amygdala, cingulate cortex and the thalamus. $I_h$ currents appear to be preferentially expressed by medium/large DRGs and may be absent from the somata of most C-type (small) DRGs (Scroggs et al., J Neurophysiol. 71: 271-279; Tu et al., J Neurosci. Res. 2004 76:713-722). Furthermore, it has been reported that nerve injury in rats (Chung model) increased $I_h$ current density in large DRGs and caused pacemaker-driven, spontaneous action potentials in the ligated nerve. ZD 7288, an $I_h$ channel blocker, reduced the firing frequency of ectopic discharges in A-beta and A-delta fibres, without causing conduction block (Lee et al 2005 J Pain 417-424). Intraperitoneal administration of an $I_h$ blocker, ZD 7288, in a model of neuropathic pain, dose-dependently reverses mechanical allodynia (Chung/von Frey; Chaplan, et al 2003 J Neurosci. 23: 1169-1178). ZD 7288 also suppresses allodynia in the rat CFA model of inflammatory pain and blocks spontaneous pain in a rat, mild thermal injury model. Another research group has reported that local administration of ZD 7288 to the sciatic nerve 4 h after surgery in rats attenuates mechanical allodynia in the Brennan model (Dalle & Eisenach 2005 Reg. Anesth. and Pain Med 243-248).

It is hypothesised that, during chronic painful conditions, primary afferents become hyperexcitable due to peripheral sensitisation after inflammation, and a change of ion channel expression at the site of nerve damage associated with neuropathy. ZD 7288-induced inhibition of $I_h$ reduces spontaneous activity in nerve injured myelinated DRG (Yagi et al, 2000 Proc 9th World Congress on Pain 109-117) so reducing the associated pain. Current preclinical data indicate that $I_h$ channel blockers will have utility in the treatment of chronic neuropathic pain.

Currently available HCN blockers seem to inhibit all HCN isoforms with no apparent subtype selectivity, thereby limiting their utility for non-cardiac indications such as pain (Wickenden et al. "*HCN pacemaker channels and pain: a drug discovery perspective*", Current Pharm. Design 2009, 15, 2149-2169).

There remains a need for additional $I_h$ channel inhibitors that would be useful in the treatment of pain, such as neuropathic or inflammatory pain.

To this end the present invention provides amino-heteroaryl derivatives having the general Formula I

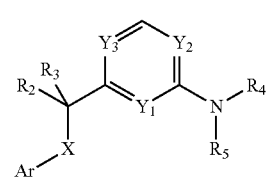

Formula 1 wherein
Ar represents phenyl or a 6-membered heteroaryl group containing 1 or 2 nitrogen atoms, each of which optionally substituted with one or more substituents selected from halogen, $(C_{1-4})$alkyl, halo$(C_{1-4})$alkyl, $(C_{1-4})$alkyloxy, halo$(C_{1-4}$alkyloxy, CN, $(C_{1-4})$alkylthio and halo$(C_{1-4})$alkylthio;
X is O, S, or $NR_1$;
$R_1$ is H or $(C_{1-4})$alkyl;
$R_2$ is $(C_{1-4})$alkyl, halo$(C_{1-4})$alkyl, $(C_{1-4})$alkyloxy$(C_{1-4})$alkyl or halo$(C_{1-4})$alkyloxy$(C_{1-4})$alkyl;
$R_3$ is H, halo$(C_{1-4})$alkyl, $(C_{1-4})$alkyloxy$(C_{1-4})$alkyl or halo$(C_{1-4})$alkyloxy$(C_{1-4})$alkyl; or
$R_2$ and $R_3$ form together with the carbon atom to which they are bonded a 3-7 membered saturated ring optionally containing an oxygen atom;
$Y_1$, $Y_2$ and $Y_3$ are independently CH or N; with the proviso that at least one of $Y_1$, $Y_2$ and
$Y_3$ is N and that when $Y_3$ is N, $Y_2$ is N;
$R_4$ and $R_5$ are independently H, $(C_{1-4})$alkyl, halo$(C_{1-4})$alkyl, $(C_{1-4})$alkyloxy$(C_{1-4})$alkyl; or
$R_4$ and $R_5$ form together with the nitrogen to which they are bonded a 3-7 membered saturated ring optionally containing an oxygen atom; or a pharmaceutically acceptable salt thereof, for use in the treatment of pain, such as neuropathic or inflammatory pain.

Another aspect of the invention provides amino-heteroaryl derivative according to general Formula 1

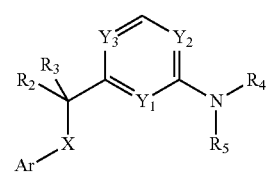

Formula 1 wherein
Ar represents phenyl or a 6-membered heteroaryl group containing 1 or 2 nitrogen atoms, each of which can be optionally substituted with one or more substituents selected from halogen, $(C_{1-4})$alkyl, halo$(C_{1-4})$alkyl, $(C_{1-4})$alkyloxy, halo$(C_{1-4})$alkyloxy, CN, $(C_{1-4})$alkylthio and halo$(C_{1-4})$alkylthio;

X is O, S, or $NR_1$;

$R_1$ is H or $(C_{1-4})$alkyl;

$R_2$ is $(C_{1-4})$alkyl, halo$(C_{1-4})$alkyl, $(C_{1-4})$alkyloxy$(C_{1-4})$alkyl or halo$(C_{1-4})$alkyloxy$(C_{1-4})$alkyl;

$R_3$ is H, $(C_{1-4})$alkyl, halo$(C_{1-4})$alkyl, $(C_{1-4})$alkyloxy$(C_{1-4})$alkyl or halo$(C_{1-4})$alkyloxy$(C_{1-4})$alkyl; or $R_2$ and $R_3$ form together with the carbon atom to which they are bonded a 3-7 membered saturated ring optionally containing an oxygen atom;

$Y_1$, $Y_2$ and $Y_3$ are independently CH or N; with the proviso that at least one of $Y_1$, $Y_2$ and $Y_3$ is N and that when $Y_3$ is N, $Y_2$ is N;

$R_4$ and $R_5$ are independently H, $(C_{1-4})$alkyl, halo$(C_{1-4})$alkyl or $(C_{1-4})$alkyloxy$(C_{1-4})$alkyl; or $R_4$ and $R_5$ form together with the nitrogen atom to which they are bonded a 3-7 membered saturated ring optionally containing an oxygen atom; or a pharmaceutically acceptable salt thereof; with the exclusion of 4-(1-{[3-chloro-5-(trifluoromethyl)-2-pyridinyl]sulfanyl}ethyl)-2-pyrimidinamine, and of the compounds of Formula I wherein Ar is phenyl; X is O; $R_2$ is $CH_3$; $R_3$, $R_4$ and $R_5$ are H; $Y_1$ is N; $Y_2$ is N; and $Y_3$ is CH.

The proviso relates to the disclosure of 4-[1-(4-chlorophenoxy)ethyl]-2-pyrimidinamine in WO 2008/067389 (ALSGEN Inc.) as a compound useful in the prevention or treatment of the symptoms of amyotrophic lateral sclerosis (ALS), and to the disclosure of 4-(1-phenoxyethyl)-2-pyrimidinamine, 4-[1-[3-(trifluoromethyl)phenoxy]ethyl]-2-pyrimidinamine, 4-[1-(2,4-dichlorophenoxy)ethyl]-2-pyrimidinamine and 4-(1-{[3-chloro-5-(trifluoromethyl)-2-pyridinyl]sulfanyl}ethyl)-2-pyrimidinamine as compounds available in screening libraries, but without a known pharmaceutical utility.

The term $(C_{1-4})$alkyl as used in the definition of Formula I means a branched or unbranched alkyl group having 1-4 carbon atoms, like butyl, isobutyl, tertiary butyl, propyl, isopropyl, ethyl and methyl. Preferred is methyl.

The term halogen means F, Cl, Br or I. A preferred halogen is F.

In the term halo$(C_{1-4})$alkyl halo means 1 or more halogen substituents. A preferred halo$(C_{1-4})$alkyl is trifluoromethyl.

In the term halo$(C_{1-4})$alkyloxy halo means 1 or more halogen substituents A preferred halo$(C_{1-4})$alkyloxy is trifluoromethyloxy.

Preferred are amino-heteroaryl derivatives of formula I wherein Ar represents phenyl or a 6-membered heteroaryl group selected from pyridin-2-yl, pyridin-3-yl, pyridin-4-yl, pyrazin-2-yl and pyrimidin-2-yl.

Also preferred are the compounds of formula I wherein $Y_1$ and $Y_2$ are N and $Y_3$ is CH.

Further preferred are compounds of formula I wherein $R_2$ is $CH_3$ and $R_3$ is H. More preferred are the compounds wherein in addition $R_4$ and $R_5$ are H.

Specifically preferred amino-heteroaryl derivatives of the invention for use in the treatment of pain, such as neuropathic and inflammatory pain, are selected from (R)-4-(1-(3-fluorophenoxy)ethyl)pyrimidin-2-amine;
(R)-4-(1-(2-chloro-5-fluorophenoxy)ethyl)pyrimidin-2-amine;
(R)-4-(1-(2,5-difluorophenoxy)ethyl)pyrimidin-2-amine;
(R)-4-(1-(2,4-difluorophenoxy)ethyl)pyrimidin-2-amine;
(R)-4-(1-(3-methoxypyridin-2-yloxy)ethyl)pyrimidin-2-amine;
(S)-4-(1-(3-fluorophenoxy)ethyl)pyrimidin-2-amine;
(S)-4-(1-(2,5-difluorophenoxy)ethyl)pyrimidin-2-amine;
(4-(1-(3-(trifluoromethyl)pyridin-2-ylthio)ethyl)pyrimidin-2-amine;
(R)-4-(1-(3-(trifluoromethyl)pyridin-2-yloxy)ethyl)pyrimidin-2-amine;
(R)-4-(1-(4-(trifluoromethyl)pyridin-2-yloxy)ethyl)pyrimidin-2-amine; and
4-(1-(3-(trifluoromethyl)pyridin-2-ylamino)ethyl)pyrimidin-2-amine;

or a pharmaceutically acceptable salt thereof.

Specifically preferred amino-heteroaryl derivatives of the invention are:

(R)-4-(1-(3-methoxypyridin-2-yloxy)ethyl)pyrimidin-2-amine;
(4-(1-(3-(trifluoromethyl)pyridin-2-ylthio)ethyl)pyrimidin-2-amine;
(R)-4-(1-(3-(trifluoromethyl)pyridin-2-yloxy)ethyl)pyrimidin-2-amine;
(R)-4-(1-(4-(trifluoromethyl)pyridin-2-yloxy)ethyl)pyrimidin-2-amine; and
4-(1-(3-(trifluoromethyl)pyridin-2-ylamino)ethyl)pyrimidin-2-amine;

or a pharmaceutically acceptable salt thereof.

The amino-heteroaryl derivatives of the invention may be prepared by methods known in the art of organic chemistry in general.

An amino-heteroaryl derivative of Formula 1 can for example be prepared from an appropriate compound of Formula 2, (Scheme 1) wherein X, $Y_1$-$Y_3$ and $R_2$-$R_5$ have the meanings as previously defined. Compounds of Formula 1 where X is O or S can be prepared from a compound of Formula 2 where X is P using a reagent Ar—XH, wherein X is O or S and Ar has the meaning as previously defined, using Mitsunobu coupling conditions (i.e. a trialkyl or aryl phosphine in the presence of a dialkyl azadicarboxylate in a solvent such as tetrahydrofuran). Compounds of Formula 1 where X is O or S can also prepared from compounds of Formula 2 where X is O or S using a reagent Ar—X', wherein X' is a leaving group such as fluoro, chloro, methanesulfonyl or a nitro group. Such transformations are typically conducted in a polar aprotic solvent such as N-methylpyrrolidinone (NMP) or tetrahydrofuran (THF) using a base such as sodium hydride.

Scheme 1

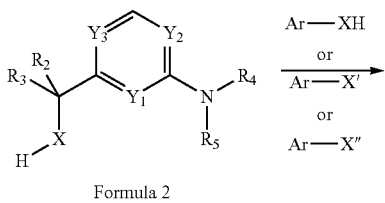

Formula 2

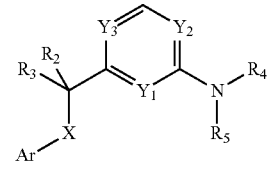

Formula 1

An amino-heteroaryl derivative of Formula 1 wherein X is $NR_1$ and $R_1$ is H or $(C_{1-4})$alkyl, can be prepared from a compound of Formula 2 where X is $NR_1$ using a reagent of Formula Ar—X', where X' is leaving group such as fluoro, chloro or a nitro group, in the presence of a base such as triethylamine or by a transition metal-catalysed reaction with a reagent of Formula Ar—X", where X" is a group that oxidatively adds to a low valency metal species, such as chloro, bromo, iodo and trifluoromethanesulfonyl.

Compounds of Formula 2 can be prepared as outlined in Scheme 2. Reduction of compounds of Formula 3 where $R_2$ is as defined above by hydrogenation in the presence of a suitable catalyst or by a metal hydride reagent such as sodium borohydride or lithium aluminium hydride gives compounds of Formula 2 where X is O and $R_3$ is H. The reaction of a compound of Formula 3 where $R_2$ is as defined above with an organometallic reagent of general formula $R_3$-Metal where $R_3$ has the definitions above and Metal is a species such as lithium, trialkylsilyl or a magnesium halide moiety gives alcohol compounds of Formula 2 where X is O.

The use of a chiral reagent or catalyst to perform the hydride addition, hydrogenation or alkyl-bearing organometallic reagent addition can give compounds of Formula 2 that are optically enriched with one stereoisomer.

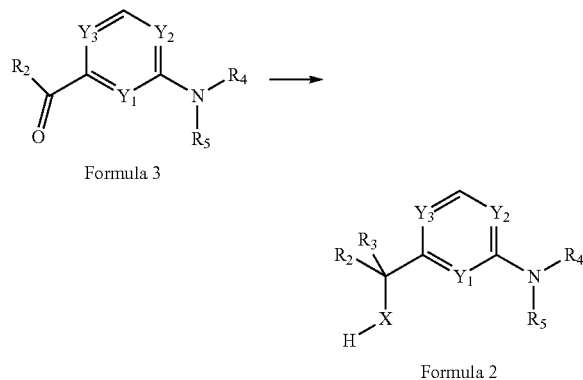

Compounds of Formula 2 where X is $NR_1$, wherein $R_1$ is $(C_{1-4})$alkyl, can be prepared as outlined in Scheme 3. Condensing a compound of Formula 3 with an amine species of general Formula $R_1NH_2$ in the presence of a dehydrating agent such as magnesium sulfate or titanium tetraisopropoxide yields an imine intermediate of Formula 4 that can be reduced with a metal hydride reagent or by hydrogenation or can be treated with an organometallic reagent of Formula $R_3$-Metal to give the compound of Formula 2.

Scheme 3

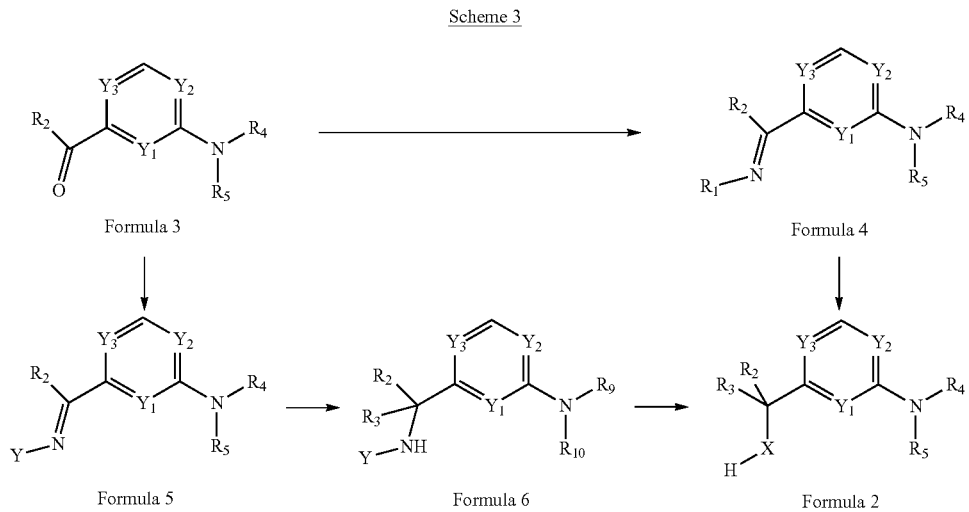

Compounds of Formula 2 where X is $NR_1$ and $R_1$ is H can be prepared as outlined in Scheme 3 by condensing a compound of Formula 3 with an amine species of general Formula $YNH_2$ where Y is a group such as a hydroxyl or a sulfinyl group of Formula $SOR_6$ where $R_6$ is an alkyl or optionally substituted aryl group in the presence of a dehydrating agent such as magnesium sulfate or titanium tetraisopropoxide to yield an imine intermediate of Formula 5 that can be directly reduced with a metal hydride reagent or by hydrogenation or treatment with an organometallic reagent of formula $R_3$-Metal with concomitant Y group removal (i.e. avoiding isolation of compounds of Formula 6) or followed by suitable Y group removal step to give the compound of Formula 2. Such a route may go via the intermediary compounds of Formula 6 which, when Y is a chiral group with one pure configuration (e.g. $SOR_6$), can allow for the separation of diastereomers and, therefore, single enantiomer compounds of Formula 2 where X is NR1.

Compounds of Formula 2 where X is $NR_1$ and $R_1$ is H can be converted to compounds of Formula 2 where X is $NR_1$ and $R_1$ is $(C_{1-4})$alkyl by reductive amination with a suitable $(C_{1-4})$ carbonyl-containing reagent in the presence of a reducing agent such as sodium triacetoxyborohydride or by reaction with a group of Formula $R_1X'$, where X' has been defined above, in the presence of a base such as triethylamine.

In an alternative method an amino-heteroaryl derivative of Formula 1 can be prepared from an appropriate compound of Formula 7, where X' is chloro, bromo or nitro, by performing an N-arylation reaction with a reagent of general formula $HNR_4R_5$ wherein $R_4$ and $R_5$ are defined above as outlined in Scheme 4. Using a reagent of Formula 7 where X' is defined above in Scheme 4. Such an $S_NAr$ reaction can require the presence of a base such as triethylamine.

Scheme 4

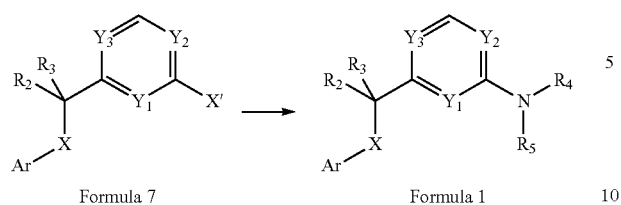

Compounds of Formula 1 can be prepared from an appropriate compound of Formula 8 where X" is defined above by performing an N-arylation reaction with a reagent of general formula $HNR_4R_5$ as outlined in Scheme 5. The reaction is performed by using suitable transition metal-catalysed N-arylation.

Scheme 5

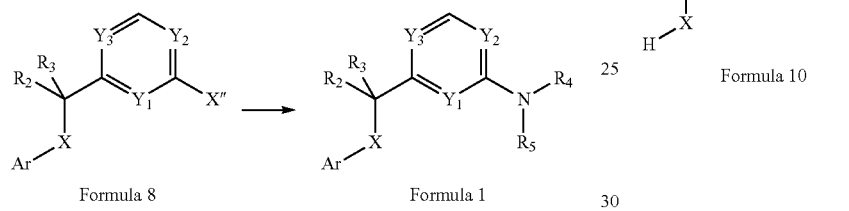

Compounds of Formula 7 can be prepared as outlined in Scheme 6, using transformations analogous to those described in Scheme 1, starting from compounds of Formula 9. In a similar way, compounds of Formula 8 can be prepared as outlined in Scheme 7 starting from compounds of Formula 10.

Scheme 6

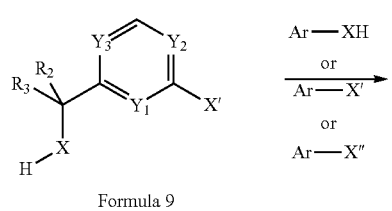

Scheme 7

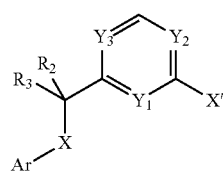

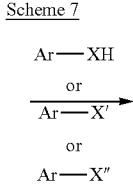

Compounds of Formula 9 where X is O can be prepared from compounds of Formula 11 as outlined in Scheme 8 by reduction using a suitable reducing agent or reaction with an organometallic reagent of Formula $R_3$-Metal. In a similar manner, compounds of Formula 10 can be prepared from compounds of Formula 15 as outlined in Scheme 9. Compounds of Formula 9 and 10 where X is $NR_1$ can be prepared as outlined in Schemes 8 and 9 respectively using analogous transformations to those described in Scheme 3.

Scheme 8

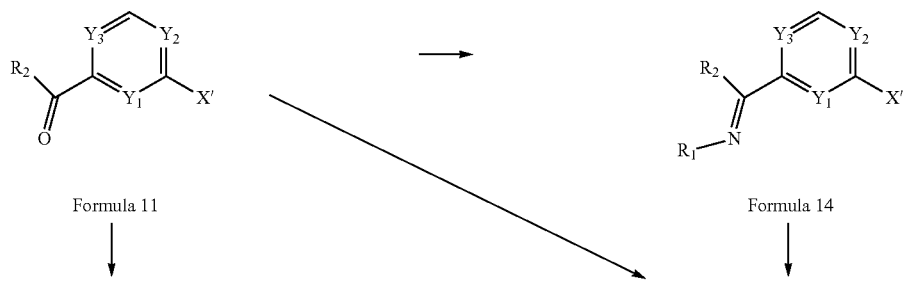

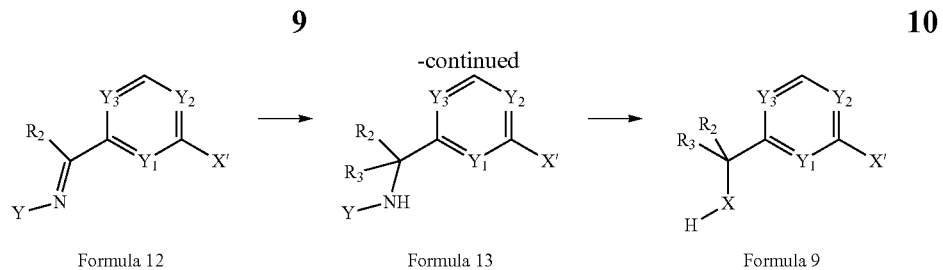

Formula 12 → Formula 13 → Formula 9

Scheme 9

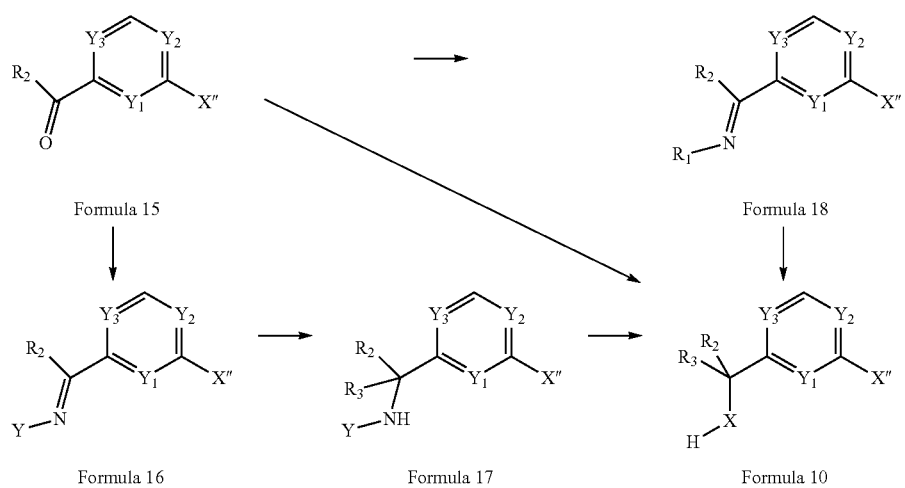

Formula 15, Formula 18, Formula 16, Formula 17, Formula 10

Compounds of Formula 11 and Formula 15 where $R_2$ is defined as above can be prepared from enol ether compounds of Formula 20 and 22 respectively as outlined in Schemes 10 and 11, respectively. Cross coupling compounds of Formula 19 and 21 respectively with a vinyl metal species of Formula 23 where M is a metallic species such as trialkylstannane (e.g. tri-n-butyl tin) and $R_7$ and $R_8$ are independently selected from H, $(C_{1-3})$alkyl, halo$(C_{1-3})$alkyl, $(C_{1-3})$alkyloxy$(C_{1-4})$alkyl and halo$(C_{1-3})$alkyloxy$(C_{1-4})$alkyl with the proviso that no more than four carbons atoms are contiguously linked through to the carbon atom bearing both the $R_7$ and $R_8$ groups and $R_9$ is an alkyl or trialkylsilyl group, yields compounds of Formula 20 and Formula 22 respectively. Subsequent acidic hydrolysis of the enol ethers of Formula 20 and Formula 22 respectively gives the desired intermediates of formula 11 and formula 15, respectively.

-continued

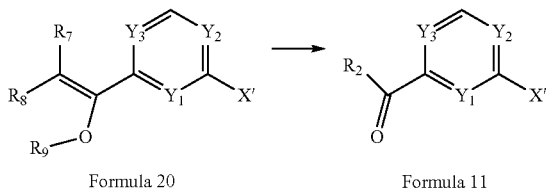

Formula 20, Formula 11

Scheme 10

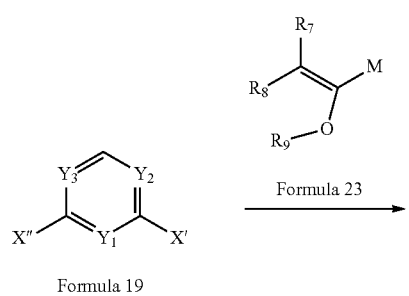

Formula 19

Scheme 11

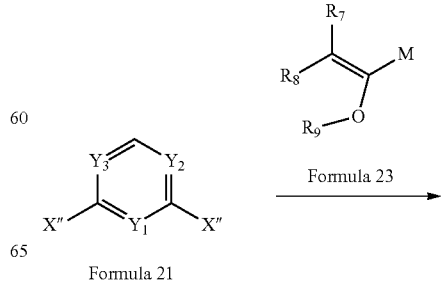

Formula 21

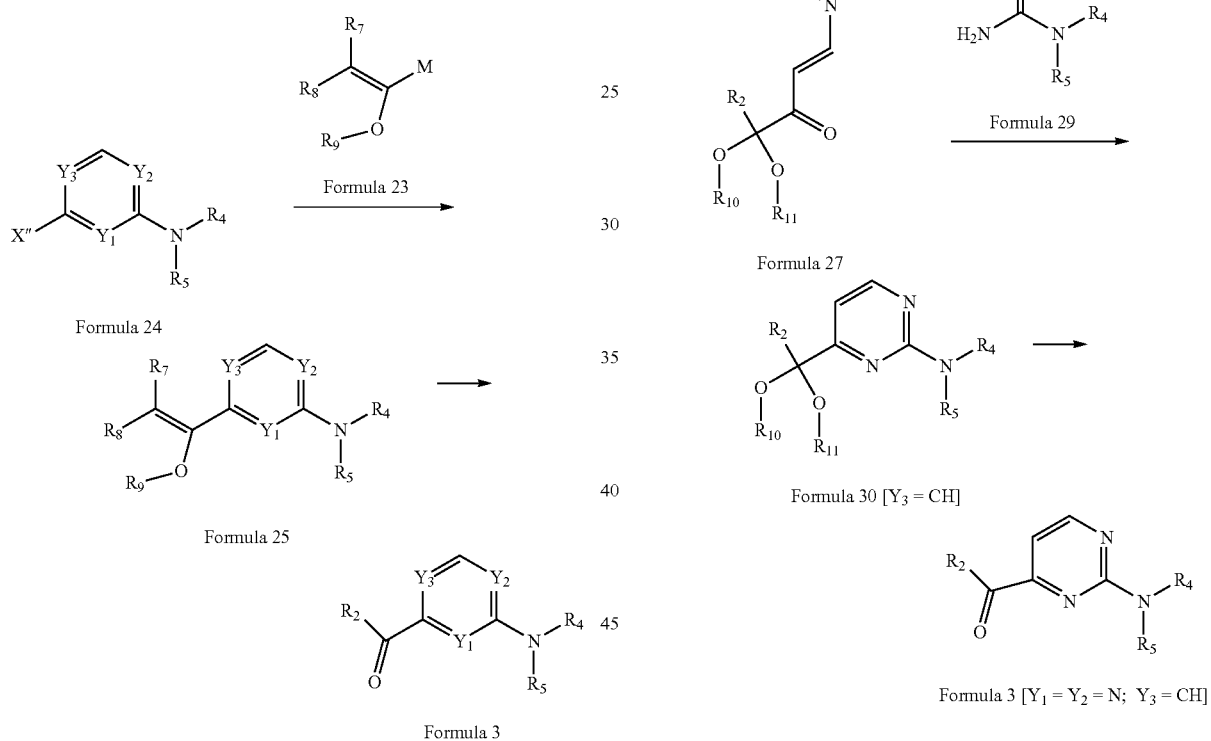

Compounds of Formula 3 where $R_2$ is defined as above can be prepared from enol ether compounds of Formula 25 as outlined in Scheme 12 by cross coupling compounds of Formula 24 with a vinyl metal species of Formula 23 where M, $R_7$, $R_8$, and $R_9$ is defined above to give enol ether compounds of Formula 25. Subsequent acidic hydrolysis of the enol ether compounds of Formula 25 gives the desired carbonyl compound of Formula 3.

Compounds of Formula 3 where $Y_1$ and $Y_2$ are N and $Y_3$ is CH can be prepared starting from monoacetal protected diketones of formula 26 where $R_2$ is defined as above and $R_{10}$ and $R_{11}$ are independently $(C_{1-10})$alkyl groups (e.g. methyl or ethyl) or both $R_{10}$ and $R_{11}$ are bonded together to give a $(C_{2-10})$alkylidene group (e.g. ethylene) as outlined in Scheme 13. Condensing a compound of Formula 26 with a compound of Formula 28 where $R_{12}$ and $R_{13}$ are independently $(C_{1-10})$ alkyl groups (e.g. methyl or ethyl) or both $R_{12}$ and $R_{13}$ are bonded together to give a $(C_{2-10})$alkylidene group (e.g. butylene) and $R_{14}$ and $R_{15}$ are independently $(C_{1-10})$alkyl groups (e.g. methyl or ethyl) or both $R_{14}$ and $R_{15}$ are bonded together to give a $(C_{2-10})$alkylidene group (e.g. butylene) gives an enamine compound of Formula 27. Condensing a compound of Formula 27 with an amidine of Formula 29 where $R_4$ and $R_5$ are defined above gives a pyrimidine of Formula 30.

Acidic hydrolysis of a compound of Formula 30 with for example an acid such as hydrochloric acid gives a compound of Formula 3 where $Y_3$ is CH, $Y_1$ and $Y_2$ are N and $R_2$, $R_4$ and $R_5$ are as defined above.

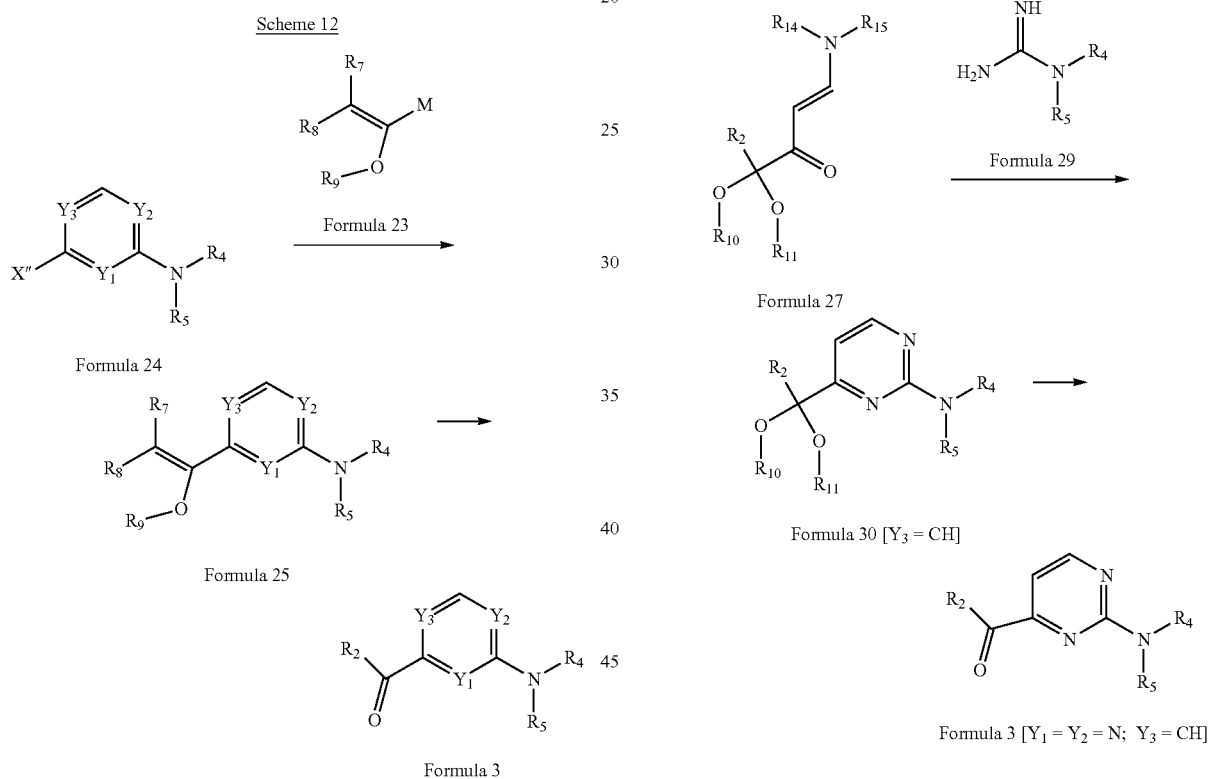

Some of the transformations described above can be performed using analogous intermediates that have heteroatoms protected by means of protecting groups as outlined in Scheme 14.

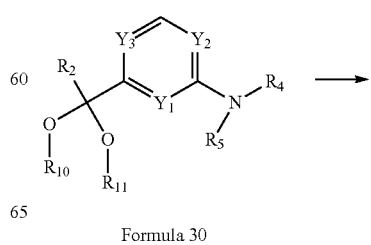

-continued

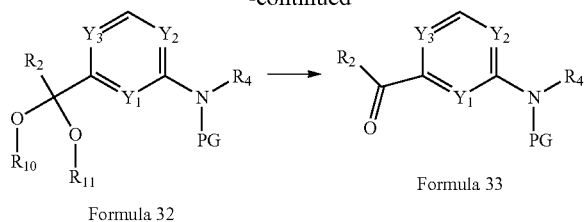

Formula 32    Formula 33

For example the compounds of Formula 30 where $R_5$ is H can be converted to compounds of Formula 32 where $R_2$, $Y_1$ to $Y_3$, $R_4$, $R_{10}$ and $R_{11}$ are as defined above and PG is a protecting group that can include, but is not limited to tert-butyloxycarbonyl (Boc) and benzyloxycarbonyl (Cbz) groups. Selective hydrolysis of the acetal function gives compounds of Formula 33. The use of such protecting groups is well described in Wuts P. G. M and Greene T. W. 'Protecting Groups in Organic Synthesis' New York, Wiley (2006). Using the same routes as described in Schemes 1, 2, 3 and 12 the same products can be prepared by the addition of a deprotection step starting from compounds of Formula 33.

Amino-heteroaryl derivatives of Formula 1 wherein $R_2$ and $R_3$ have the meanings as previously defined and $Y_3$ is CH can be prepared as outlined in Scheme 15. Reaction of a compound of Formula 34a, where $R_{16}$ is H, alkyloxy or aryloxy, with a compound of Ar—X' or Ar—X" in a manner analogous to that described in Scheme 7 followed by, where necessary, suitable functional group interconversion to convert $R_{16}$ to H gives compounds of Formula 35. Alternatively reaction of a compound of Formula 34b with a compound of Ar—XH followed by, where necessary, suitable functional group interconversion to convert $R_{16}$ to H gives compounds of Formula 35. Treatment of a compound of Formula 35 with an organometallic species of general formula $CH_3$-Metal, wherein Metal has the meaning as above, gives compounds of Formula 36 which can be oxidised to compounds of Formula 37. Condensation of compounds of Formula 35 with a reagent of Formula 28, where $R_{12}$, $R_{13}$, $R_{14}$ and $R_{15}$ have the meanings above, gives enamine compounds of Formula 38 which when condensed with compounds of Formula 29 gives compounds of Formula 1.

Scheme 15

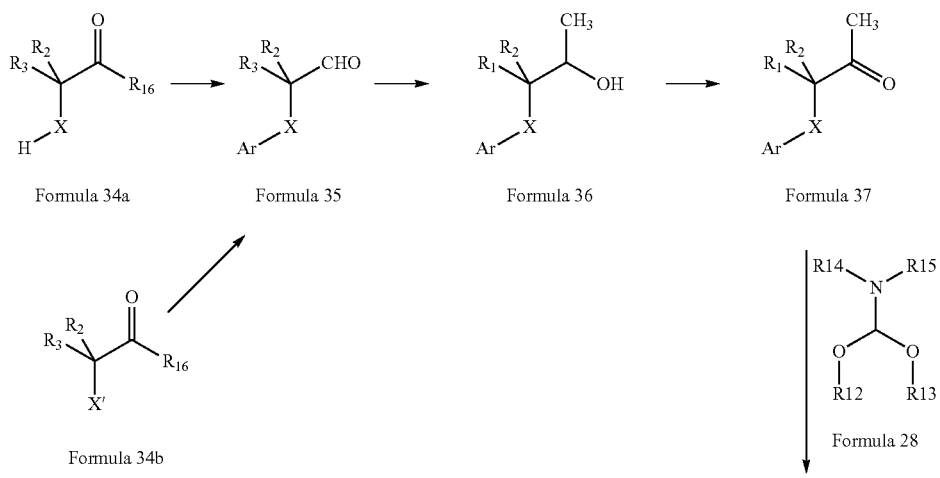

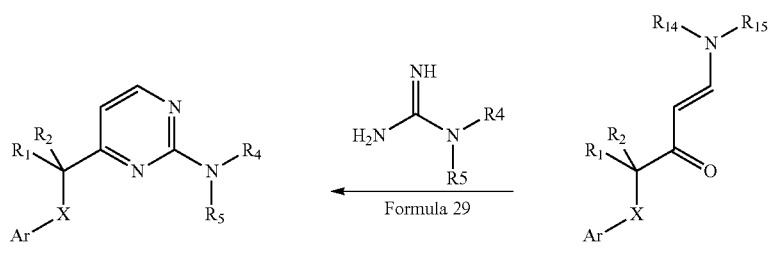

Scheme 16

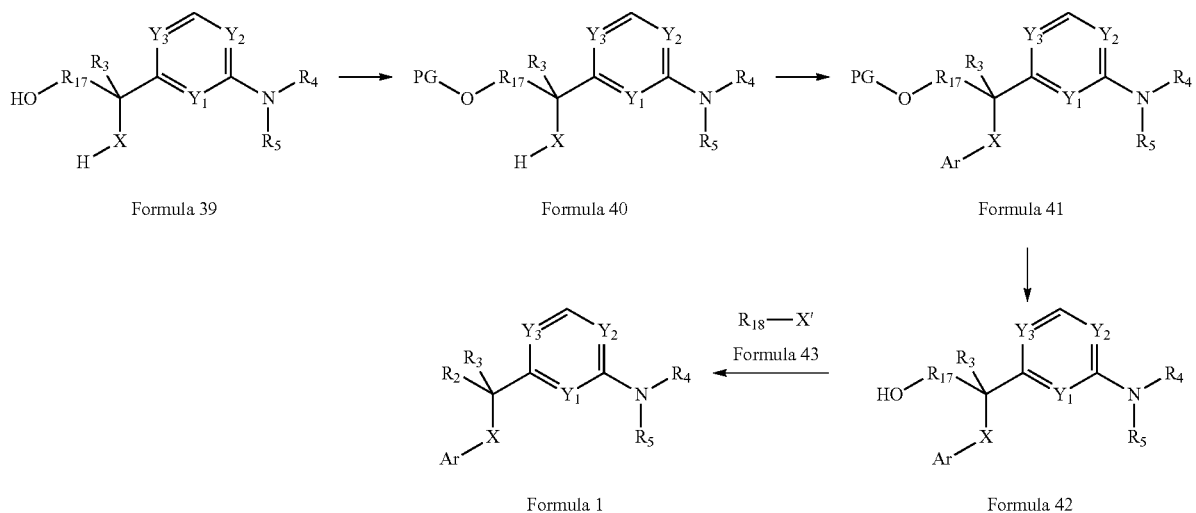

Compounds of Formula 1 where $R_2$ is a $(C_{1-4})$alkyloxy $(C_{1-4})$alkyl or halo$(C_{1-4})$alkyloxy-$(C_{1-4})$alkyl can be prepared as outlined in Scheme 16 starting from a compound of Formula 39 where $R_{17}$ is a $(C_{1-4})$alkylene group. Mono protection of the hydroxy group with a suitable protecting group gives a compound of Formula 40 where PG is a protecting group such as, but not limited to, tert-butyldimethyl silyl. Reaction of a compound of Formula 40 with a suitable reagent of Formula Ar—XH, Ar—X' or Ar—X" (see Schemes 6 and 7) using conditions outlined above in Scheme 1 gives compounds of Formula 41. Removal of the protecting group gives compounds of Formula 42 and O-alkylation with a reagent of Formula 43 where $R_{18}$ is a $(C_{1-4})$alkyl or halo $(C_{1-4})$alkyl gives compounds of Formula 1. Modification of this route whereby $R_5$ is replaced by a suitable protecting group that is orthogonal to the group PG bonded to the oxygen is possible in an analogous fashion to that outlined in Scheme 14. Such protecting group strategies are well known to those skilled in the art.

Scheme 17

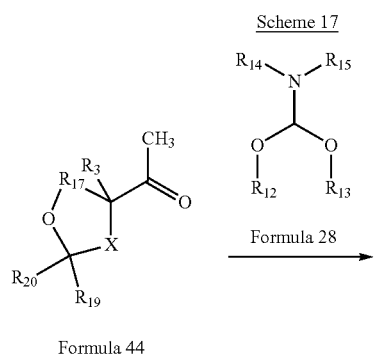

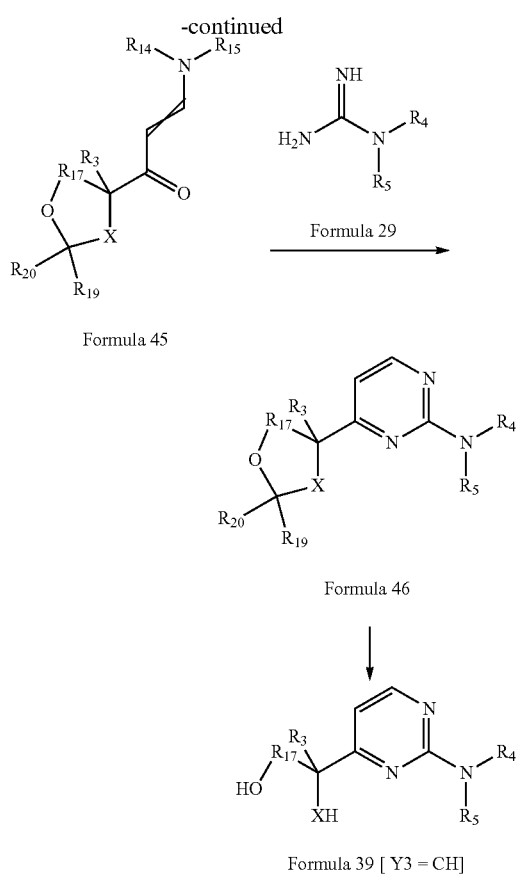

Compounds of Formula 39 wherein X is O and $Y_3$ is CH can be prepared from compounds of Formula 44 where $R_{19}$ and $R_{20}$ are independently $(C_{1-10})$alkyl groups (e.g. methyl or ethyl) or both $R_{19}$ and $R_{20}$ are bonded together to give a $(C_{2-10})$alkylidene group as outlined in Scheme 17 in an analogous sequence to that outlined in Schemes 13 and 15. Reaction of a compound of Formula 44 where $R_3$, $R_{17}$, $R_{19}$ and $R_{20}$ have been defined above and X is O with a reagent of Formula 28 gives a compound of Formula 45. Subsequent treatment with a reagent of Formula 29 gives compounds of Formula 46 which are deprotected with, for example an acid such as hydrochloric acid to give compounds of Formula 39 where X is O.

Scheme 18

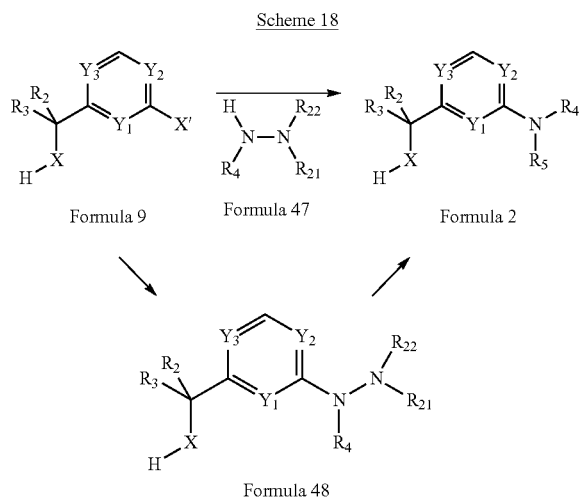

Compounds of Formula 2 can be prepared by the direct displacement of the group X' from compounds of Formula 9 where X' is defined above by an amine of general formula $HNR_4R_5$ where $R_4$ and $R_5$ are defined above as outlined in Scheme 18. Alternatively displacement of the X' group can be effected with the use of a hydrazine reagent of Formula 47 where $R_4$ is defined above and $R_{21}$ and $R_{22}$ can be H, an alkyl or an aryl group to give compounds of Formula 48. Fission of the nitrogen-nitrogen bond using, for example, Raney nickel gives compounds of Formula 2 where $R_4$ is defined above and $R_5$ is H.

Scheme 19.

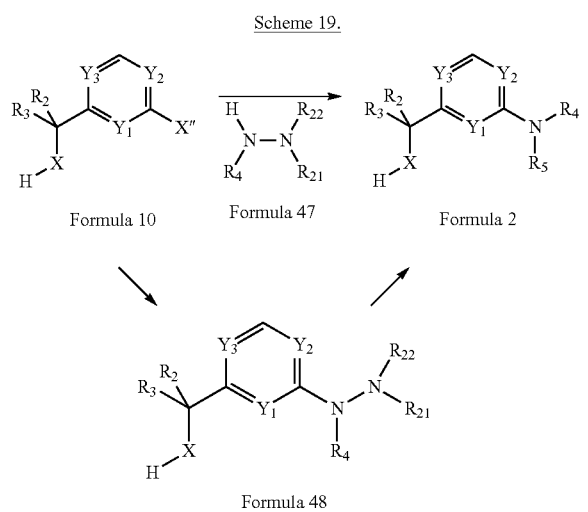

The analogous sequence of reactions can be performed starting from a compound of Formula 10 whereby the N-arylation reaction with a reagent of general formula $HNR_4R_5$ or Formula 47 is performed using a transition metal catalyst as outlined in Scheme 19.

Compounds of Formula 2 where $R_4$ and $R_5$ are both H can be prepared from a compound of Formula 10 by the N-arylation of an imine of Formula 49 where $R_{23}$ and $R_{24}$ are independently phenyl or optionally substituted phenyl rings by the use of a transition metal catalyst for example tetrakis(triphenylphosphine)palladium (0) to give a compound of Formula 50 as outlined in Scheme 20. Hydrolysis of the imine functionality gives compounds of Formula 2 where $R_4$ and $R_5$ are both H. Alternatively compounds of Formula 1 can be prepared directly from compounds of Formula 48 by installation of the Ar group followed by hydrolysis of the benzophenone imine.

The reagent of general formula $HNR_4R_5$ can be substituted by a reagent of Formula 47 in Scheme 4 leading to compounds of Formula 1 in an analogous sequence to that outlined in Scheme 18. Similarly the reagents of Formula 46 and Formula 47 can substitute the reagent of $HNR_4R_5$ in Scheme 5 leading to compounds of Formula 1 in an analogous sequence to that outlined in Scheme 19 and Scheme 20.

Scheme 20

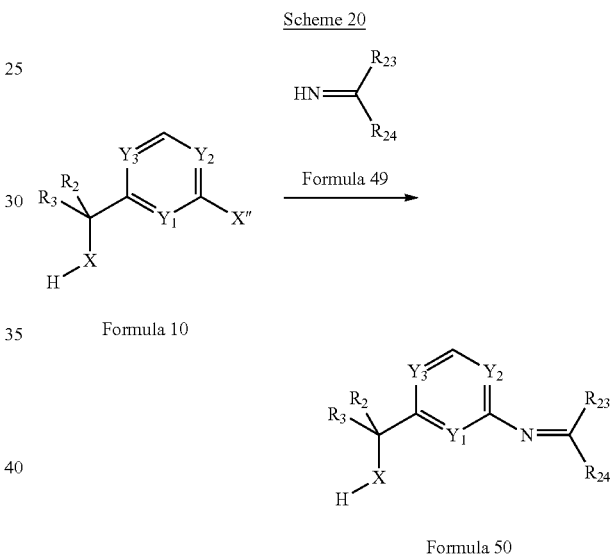

Compounds of Formula 1 where $Y_1$, $Y_2$ and $Y_3$ are all N and $R_4$ and $R_5$ are both H can be prepared by reacting an amidine of Formula 51 with a dialkylcyanocarbonimidodithioate of Formula 52 where $R_{25}$ is an alkyl group to give an aminothioalkyl-1,3,5-triazine of Formula 53 as outlined in Scheme 21, to which an aromatic moiety is coupled, using one of the methods outlined above, to provide compounds of Formula 54. Removal of the thioalkyl group from compounds of Formula 54 using for example Raney Nickel gives compounds of Formula 1 where $Y_1$, $Y_2$ and $Y_3$ are all N and $R_4$ and $R_5$ are both H.

Scheme 21

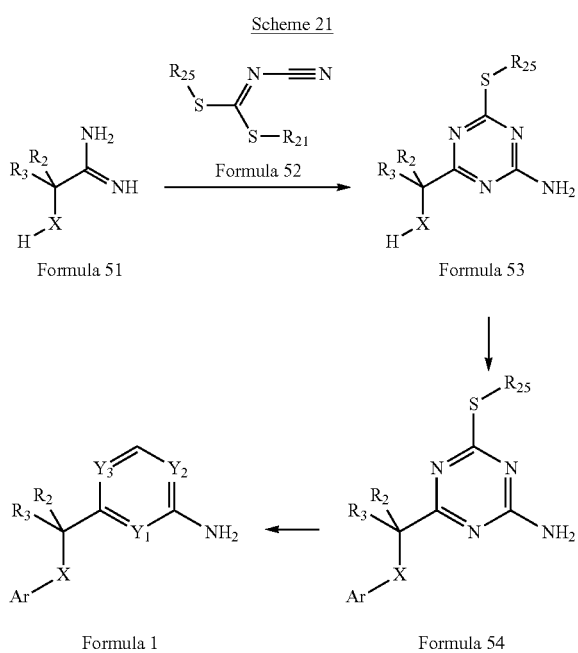

Compounds of Formula 3 where $R_2$ is defined above can be prepared by the addition of an organometallic reagent of general formula $R_2$-Metal or a hydride reducing agent to a compound of Formula 55 where E is a suitable electrophilic precursor group to a ketone or aldehyde, such as a nitrile or an amide functionality such as a Weinreb amide as outlined in Scheme 22. In analogous fashion, compounds of Formula 11, Formula 15 and Formula 33 can be prepared.

Scheme 22

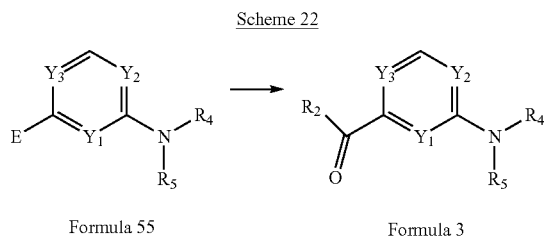

The amino-heteroaryl derivatives of the invention according to Formula I may contain one or more centres of chirality, and may exist therefore as stereoisomers, including diastereomers. The present invention includes the aforementioned stereoisomers within its scope and each of the individual R, S, R/S and S/S isomers of the compounds of Formula I and their salts, substantially free, i.e. associated with less than 5%, preferably less than 2%, in particular less than 1% of another stereoisomer, and mixtures of such stereoisomers in any proportions.

Purified stereoisomers can be obtained using methods such as cystallisation of chiral salt forms, chiral chromatographic resolution or resolution using enzymatic methods. Such methods are well known to those skilled in the art. Methods described in 'Advanced Organic Chemistry' (March J., New York, Wiley (1985) and in "Chirality in Industry" (Edited by A. N. Collins, G. N. Sheldrake and J. Cosby, 1992; John Wiley) may be used.

The present invention also embraces isotopically-labelled amino-heteroaryl derivatives of Formula I of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, sulphur, phosphorus, fluorine and chlorine, such as $^2$H, $^3$H, $^{13}$C, $^{14}$C, $^{15}$N, $^{18}$O, $^{17}$O, $^{18}$F, $^{35}$S and $^{36}$Cl, respectively. Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Pharmaceutically acceptable salts may be obtained by treating a free base of a compound of Formula I with a mineral acid such as hydrochloric acid, hydrobromic acid, phosphoric acid and sulfuric acid, or an organic acid such as for example ascorbic acid, citric acid, tartaric acid, lactic acid, maleic acid, malonic acid, fumaric acid, glycolic acid, succinic acid, propionic acid, acetic acid and methane sulfonic acid. Preferred are the salts obtained by hydrochloric acid and L-(+)-tartaric acid.

The amino-heteroaryl derivatives of the invention may exist in unsolvated as well as in solvated forms with pharmaceutically acceptable solvents such as water, ethanol and the like. In general, the solvated forms are considered equivalent to the unsolvated forms for the purpose of the invention.

The present invention further provides pharmaceutical compositions comprising a amino-heteroaryl derivative according to general Formula I, or a pharmaceutically acceptable salt thereof, in admixture with pharmaceutically acceptable auxiliaries, and optionally other therapeutic agents. The term "acceptable" means being compatible with the other ingredients of the composition and not deleterious to the recipients thereof. Compositions include e.g. those suitable for oral, sublingual, subcutaneous, intravenous, epidural, intrathecal, intramuscular, transdermal, pulmonary, local, ocular or rectal administration, and the like, all in unit dosage forms for administration. A preferred route of administration is the oral route.

For oral administration, the active ingredient may be presented as discrete units, such as tablets, capsules, powders, granulates, solutions, suspensions, and the like. For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al, Remington: The Science and Practice of Pharmacy (20th Edition, Lippincott Williams & Wilkins, 2000, see especially Part 5: Pharmaceutical Manufacturing), the active agent may be compressed into solid dosage units, such as pills, tablets, or be processed into capsules, suppositories or patches. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as described before, in combination with packaging material suitable for said composition, said packaging material including instructions for the use of the composition for the use as described before.

The amino-heteroaryl derivatives of the invention were found to be inhibitors of the $I_h$ channel as measured by patch clamp electrophysiology using the human HCN1 channel (see international patent application WO 01/090142: "Full length human HCN1 $I_h$ channel subunits and variants"— Akzo Nobel N.V.) expressed in HEK cells. The compounds of the invention have utility in the treatment of pain which is mediated through modulation of the $I_h$ channel, preferably neuropathic or inflammatory pain, such as neuropathic pain occurring in conditions like trigeminal neuralgia, post herpetic neuralgia (pain following shingles), diabetic neuropathy, phantom limb pain following amputation, multiple sclerosis, pain following chemotherapy, fibromyalgia (chronic muscle pain disorder), HIV infection, alcoholism, cancer (as a direct result of cancer on peripheral nerves or as a side effect of some chemotherapy drugs) and atypical facial pain.

The compounds of the invention can also be used in conjunction with other drugs, for example analgesic drugs such as opioids and non-steroidal anti-inflammatory drugs (NSAIDs), including COX-2 selective inhibitors.

The compounds of the invention may be administered to humans in a sufficient amount and for a sufficient amount of time to alleviate the symptoms. Illustratively, dosage levels for humans can be in the range of 0.001-50 mg per kg body weight, preferably in a dosage of 0.01-20 mg per kg body weight.

The invention is further illustrated by the following examples.

Methods

General Chemical Procedures.

All reagents were either purchased from common commercial sources or synthesised according to literature procedures using commercial sources. Proton NMR ($^1$H NMR) were obtained on a Bruker DPX 400 spectrometer and are referenced to internal tetramethylsilane (TMS). Mass spectra were recorded on a Shimadzu LC-8A (HPLC) PE Sciex API 150EX LCMS.

Intermediate Compounds

Compound 1a: 1-(dimethylamino)-4,4-dimethoxypent-1-en-3-one

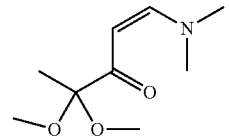

3,3-Dimethoxy-2-butanone (24.96 g) and N,N-dimethylformamide dimethyl acetal (25.09 mL) were combined and heated to 100° C. overnight. Further N,N-dimethylformamide dimethyl acetal (5 mL) was added and heating was continued for another day. The reaction mixture was concentrated in vacuo to afford 34.29 g of 4-(1,1-dimethoxyethyl)-pyrimidin-2-amine as a brown oil.

In a similar manner were prepared the following:
1b: 1-(dimethylamino)-4,4-dimethoxyhex-1-en-3-one starting from 3,3-dimethoxy-2-pentanone.
1c: 1-(dimethylamino)-4,4-dimethoxybut-1-en-3-one starting from 1,1-dimethoxy-2-propanone.
1d: 1-(2,2-Dimethyl-1,3-dioxolan-4-yl)-3-(dimethylamino)prop-2-en-1-one starting from 1-(2,2-dimethyl-1,3-dioxolan-4-yl)ethanone (prepared in two steps from 2,2-dimethyl-1,3-dioxolane-4-carboxaldehyde).

Compound 2a: 4-(1,1-dimethoxyethyl)pyrimidin-2-amine

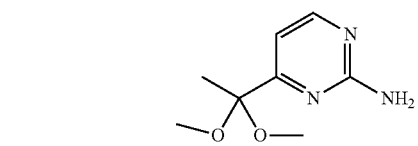

1-(dimethylamino)-4,4-dimethoxypent-1-en-3-one (1a) (34.29 g) was dissolved in ethanol (750 mL). Potassium carbonate (65.3 g) and guanidine hydrochloride (20.77 g) were added and the resulting suspension heated to reflux overnight. The reaction mixture was concentrated in vacuo, the residue was stirred with water overnight, filtered and dried in a vacuum oven at 40° C. overnight to afford the title compound (21.01 g) as a white solid. The filtrate was extracted with dichloromethane (3×700 mL) and the combined organic layers were dried over sodium sulfate and concentrated in vacuo to afford a further crop (10.6 g) of the title compound.

In a similar manner were prepared the following
2b: 4-(1,1-dimethoxypropyl)pyrimidin-2-amine starting from 1-(dimethylamino)-4,4-dimethoxyhex-1-en-3-one (1b) and guanidine hydrochloride.
2c: 4-(1,1-dimethoxymethyl)pyrimidin-2-amine starting from 1-(dimethylamino)-4,4-dimethoxybut-1-en-3-one (1c) and guanidine hydrochloride.
2d: 4-(1,1-dimethoxymethyl)-2-(N-methylamino)pyrimidine starting from 4-(1,1-dimethoxyethyl)pyrimidin-2-amine (1a) and N-methyl guanidine hydrochloride.
2e: 4-(1,1-dimethoxyethyl)-2-(pyrrolidin-1-yl)pyrimidine starting from 1-(dimethylamino)-4,4-dimethoxypent-1-en-3-one (1a) and pyrrolidine-1-carboximidamide hydroiodide.
2f: 4-(2,2-dimethyl-1,3-dioxolan-4-yl)pyrimidin-2-amine starting from 1-(2,2-Dimethyl-1,3-dioxolan-4-yl)-3-(dimethylamino)prop-2-en-1-one (1d) and guanidine hydrochloride.

Compound 3a: 1-(2-aminopyrimidin-4-yl)ethanone

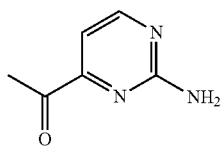

To a stirred solution of 4-(1,1-dimethoxyethyl)pyrimidin-2-amine (2a) (180 g) in tetrahydrofuran (2 L) was added 2M hydrochloric acid solution (980 mL) and stirring continued at room temperature overnight. Most of the solvent was removed in vacuo and remaining aqueous solution was poured into an aqueous saturated sodium hydrogen carbonate solution. The sandy coloured precipitate was filtered off and dried in vacuo at 40° C. to give the title compound (112 g).

In a similar manner were prepared the following:
3b: 1-(2-aminopyrimidin-4-yl)propanone starting from 4-(1,1-dimethoxypropyl)pyrimidin-2-amine (2b).
3c: 1-[2-(N-methylamino)pyrimidin-4-yl]ethanone starting from 4-(1,1-dimethoxymethyl)-2-(N-methylamino)pyrimidine (2d).
3d: 1-(2-(pyrrolidin-1-yl)pyrimidin-4-yl)ethanone starting from 4-(1,1-dimethoxyethyl)-2-(pyrrolidin-1-yl)pyrimidine (2e).

Compound 4a: 2-chloro-4-acetylpyridine

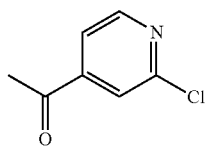

To a solution of 2-chloro-4-cyanopyridine (41.6 g) in dry ether under a nitrogen-atmosphere was added methylmagnesium iodide (200 mL, 3M in ether) dropwise. The resulting mixture was stirred at room temperature overnight. The solids which were formed were collected and poured immediately on a mixture of 1000 g ice, 500 mL water and 250 mL 6N HCl. The aqueous solution was allowed to reach room temperature and then extracted with ether (800 mL) and the combined organic layers were dried (sodium sulfate) and evaporated to give a red oil which crystallised on standing. This material was taken up in a mixture of ether (ca 300 mL) and heptane (~50 mL). The solution was cooled in an acetone/dry-ice bath which resulted in formation of yellow solids that were filtered and air-dried for 30 minutes to give the title compound (21.7 g) as a yellow solid.

Compound 5a: 1-(2-aminopyrimidin-4-yl)ethanol

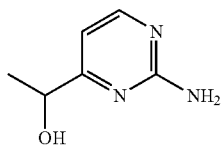

1-(2-aminopyrimidin-4-yl)ethanone (Compound 3a) (0.5 g) was dissolved in 50 mL methanol and cooled to 0° C. Sodium borohydride (0.138 g) was added portion wise and the mixture was stirred for 16 hours at room temperature. Saturated ammonium chloride solution (20 mL) was added and this mixture was extracted twice with ethyl acetate. The combined organic layers were washed with brine, dried over sodium sulfate and evaporated to give the title compound (270 mg) as a colourless oil that solidified on standing.

In a similar manner were prepared the following:
5b: 1-(2-aminopyrimidin-4-yl)propanol starting from 1-(2-aminopyrimidin-4-yl)propanone (3b).
5c: 1-[2-(N-methylamino)pyrimidin-4-yl]ethanol starting from 1-[2-(N-methylamino)-pyrimidin-4-yl]ethanone (3c).
5d: 1-(2-chloropyridin-4-yl)ethanol starting from 2-chloro-4-acetylpyridine (4a).

Compound 6a: (R)-1-(2-aminopyrimidin-4-yl)ethanol

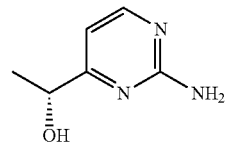

To a solution of 1-(2-aminopyrimidin-4-yl)ethanone (Compound 3a) (59.8 g) in N,N-dimethylformide (600 mL) at room temperature was added chloro[(1R,2R)—N-(p-toluenesulfonyl)-1,2-diphenyl-1,2-ethanediamine] (p-cymene) ruthenium (II) (3.35 g). The resulting dark orange solution was then purged with argon and formic acid—triethylamine complex (5:2) (189 g) was added. The reaction was stirred under an atmosphere of argon at room temperature for 1 h then evaporated to dryness under reduced pressure to yield a dark brown residue that was taken up in dichloromethane and the minimal volume of methanol and chromatographed on silica gel eluting with 4-10% methanol in dichloromethane. Fractions containing product were combined and evaporated under reduced pressure to yield the title compound (29.2 g) that was a 2.4%:97.6% ratio of enantiomers by chiral SFC (supercritical fluid chromatography) chromatography.

In a similar manner were prepared the following:
6b: (S)-1-(2-aminopyrimidin-4-yl)ethanol starting from 1-(2-aminopyrimidin-4-yl)ethanone (3a) and using chloro[(1S,2S)—N-(p-toluenesulfonyl)-1,2-diphenyl-1,2-ethanediamine] (p-cymene)ruthenium (II) as catalyst.
6c: (R)-1-(2-aminopyrimidin-4-yl)propanol starting from 1-(2-aminopyrimidin-4-yl)propanone and using chloro[(1R,2R)—N-(p-toluenesulfonyl)-1,2-diphenyl-1,2-ethanediamine] (p-cymene)ruthenium (II) as catalyst.
6d: (S)-1-(2-aminopyrimidin-4-yl)propanol starting from 1-(2-aminopyrimidin-4-yl)propanone and using chloro[(1S,2S)—N-(p-toluenesulfonyl)-1,2-diphenyl-1,2-ethanediamine] (p-cymene)ruthenium (II) as catalyst.
6e: (S)-1-(2-N-methylaminopyrimidin-4-yl)ethanol starting from 1-[2-(N-methylamino)pyrimidin-4-yl]ethanone (3c) and using chloro[(1S,2S)-N-(p-toluenesulfonyl)-1,2-diphenyl-1,2-ethanediamine] (p-cymene)ruthenium (II) as catalyst.
6f: (R)-1-(2-(pyrrolidin-1-yl)pyrimidin-4-yl)ethanol starting from 1-(2-(pyrrolidin-1-yl)pyrimidin-4-yl)ethanone (3d) and using chloro[(1R,2R)—N-(p-toluenesulfonyl)-1,2-diphenyl-1,2-ethanediamine] (p-cymene)ruthenium (II) as catalyst.

Compound 7a: 2-N-(benzyloxycarbonyl)amino-4-(1,1-dimethoxymethyl)pyrimidine

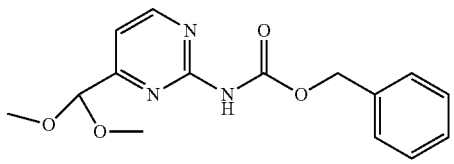 [SMILES: COC(OC)c1ccnc(NC(=O)OCc2ccccc2)n1]

To a solution of 4-(1,1-dimethoxymethyl)pyrimidin-2-amine (2c) (15 g) in tetrahydrofuran (300 mL) was added a solution of sodium carbonate (37.6 g) in water (200 mL). To this solution was added dropwise a solution of benzyl chloroformate (50.6 mL) in tetrahydrofuran (50 mL). After 3 hours at room temperature stirring was stopped and layers of the mixture were separated. The aqueous phase was extracted three times with ethyl acetate and the combined organic layers were washed with brine, dried (sodium sulfate) and concentrated under vacuum to give a yellow liquid) that was purified three times by flash chromatography (60% ethyl acetate in heptane) to give the title compound (17.95 g) as a white solid.

Compound 8a: 2-N-(benzyloxycarbonyl)amino-4-formyl-pyrimidine

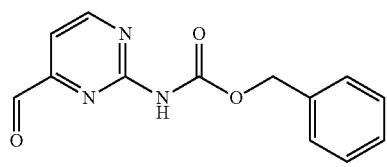 [SMILES: O=Cc1ccnc(NC(=O)OCc2ccccc2)n1]

To a solution of 2-N-(benzyloxycarbonyl)amino-4-(1,1-dimethoxymethyl)pyrimidine (7a) (17.96 g) in tetrahydrofuran (150 mL) and was added aq. HCl (1M, 150 mL) and the resulting mixture was stirred at 60° C. overnight. The acidic mixture was basified (pH>10) by addition of saturated aqueous sodium carbonate and the layers were separated with the aqueous phase extracted twice with ethyl acetate. The combined organic layers were then combined, dried (sodium sulfate) and concentrated under vacuum to give the title compound (14.1 g) as an off-white solid.

Compound 9a: 1-[2-(N-benzyloxycarbonylamino)pyrimidin-4-yl]-2,2,2-trifluoroethanol

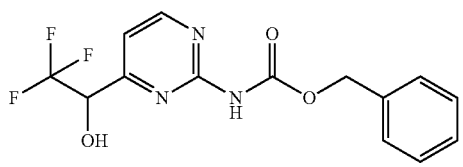 [SMILES: O=C(Nc1nccc(C(O)C(F)(F)F)n1)OCc1ccccc1]

To a solution of 2-N-(benzyloxycarbonyl)amino-4-formyl-pyrimidine (8a) (40 g) in dry N,N-dimethylformamide (800 mL) under nitrogen was added some molecular sieves. After stirring for 30 minutes, potassium carbonate (2.15 g) and trifluoromethyltrimethylsilane (26.5 g) were added and the mixture was stirred at room temperature for 16 hours. The mixture was poured onto brine (1000 mL), extracted with ethyl acetate (2×500 mL), washed with half saturated brine (2×500 mL), dried (sodium sulfate) and absorbed onto 100 g silica before being purified by gravity column chromatography (eluent: heptane/ethyl acetate 1:1) to yield the title compound (18.49 g) as an off-white solid.

Compound 10: 1-[2-aminopyrimidin-4-yl]-2,2,2-trifluoroethanol

To a solution of 1-[2-(N-benzyloxycarbonylamino)pyrimidin-4-yl]-2,2,2-trifluoroethanol (9a) in ethanol-tetrahydrofuran (1:1) (500 mL) under nitrogen-atmosphere was added palladium on carbon (785 mg). The mixture was put under a hydrogen atmosphere (balloon) and stirred at room temperature. After 45 minutes the reaction mixture was filtered through celite and concentrated under vacuum and purified by flash chromatography (dichloromethane/methanol 99:1 to 95:5) to give the title compound (1.52 g).

Compound 11a: 1-(2-aminopyrimidin-4-yl)ethanone oxime

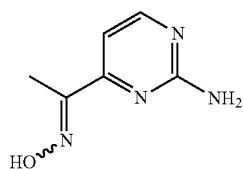

To a suspension of 1-(2-aminopyrimidin-4-yl)ethanone (3a) (4 g) in ethanol (70 mL) and water (14 mL) was added hydroxylamine hydrochloride (4.05 g) followed by sodium acetate (7.18 g) and the mixture was stirred at room temperature for one hour. After this time the reaction mixture was concentrated in vacuo, water was added and stirred for 15 minutes. The precipitate was collected by filtration and washed with water and dried in vacuo at 40° C. overnight to afford the title product (4.29 g) as a light yellow solid.

In a similar manner was prepared:
11b: 1-(2-aminopyrimidin-4-yl)propanone oxime starting from 1-(2-aminopyrimidin-4-yl)propanone (3b).

Compound 12a: 1-(2-aminopyrimidin-4-yl)ethylamine

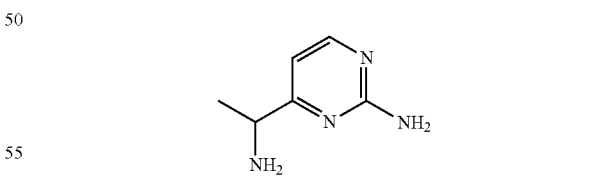

1-(2-Aminopyrimidin-4-yl)ethanone (3a) (4.29 g) was dissolved in ethanol/tetrahydrofuran (1:1, 400 mL). The suspension was saturated with argon. Raney nickel (50% slurry in water, ca 4 mL) was added and hydrogen was introduced into the flask. The reaction mixture was allowed to stir under a hydrogen atmosphere (balloon). Additional Raney nickel (50% slurry in water, ~4 mL) was added after 4 days. After the 10 days the reaction mixture was filtered over Kieselguhr and concentrated in vacuo. The residue was dissolved in ethanol/tetrahydrofuran (1:1, 150 mL) this mixture was bubbled through with argon, Raney nickel (50% slurry in water, ~4 mL) was added and the reaction mixture was put under 8 bar hydrogen pressure and stirred. After 4 days the reaction mixture was filtered over Kieselguhr and concentrated in vacuo to afford 4.4 g of a dark brown solid that was purified by column chromatography (5% triethylamine in ethyl acetate to 10% methanol in ethyl acetate) to give the title compound (1.54 g).

In a similar manner was prepared:
12b: 1-(2-aminopyrimidin-4-yl)propylamine starting from 1-(2-aminopyrimidin-4-yl)propanone oxime (11b).

Compound 13a: 1-(2-hydrazinopyridin-4-yl)ethanol

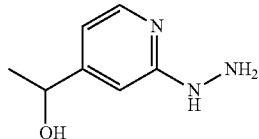

1-(2-chloropyridin-4-yl)ethanol (5d) (14.3 g) was dissolved in hydrazine hydrate (275 mL). The resulting mixture was heated at 100° C. with stirring overnight. The mixture was concentrated under vacuum to give a yellow oil that was dissolved in a small volume of methanol and ether was added, which resulted in precipitation of a white solid. The obtained suspension was stirred for 30 minutes and filtered, and the residue (hydrazine hydrochloride) was discarded. The filtrate was concentrated under vacuum to give the title compound (13.7 g) as a light-brown oil.

Compound 14a: 1-(2-aminopyridin-4-yl)ethanol

1-(2-hydrazinopyrimidin-4-yl)ethanol (13a) was dissolved in ethanol (300 mL) and Raney-Ni (35 mL, 50% slurry in water) was added. The flask was flushed with argon, put under a hydrogen atmosphere (balloon) and stirred at room temperature overnight. The mixture was filtered and concentrated under vacuum to give a red oil that was dissolved in methanol and concentrated onto silica before being purified by silica flash chromatography (100% ethyl acetate to 20% methanol in ethyl acetate) to give the title compound (9.0 g) as an orange oil.

Compound 15: 1-(4-amino-6-(methylthio)-1,3,5-triazin-2-yl)ethanol

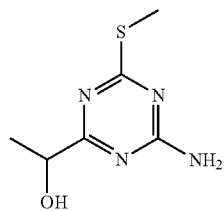

Under a nitrogen atmosphere 2-hydroxypropanimidamide hydrochloride (4.97 g) was suspended in dry N,N-dimethylformamide (25 mL) and sodium hydride (1.66 g, 60 wt % in mineral oil) was added in one portion. When gas evolution ceased the white suspension was heated to 65° C. After 1 h dimethyl cyanocarbonimidodithioate (6.24 g) was added and the mixture was stirred at 65° C. for 18 hours. The reaction mixture was concentrated and triturated with water (200 mL). The resulting precipitate was filtered off, washed with water and the aqueous layer was extracted with 5% methanol in dichloromethane (3×100 mL). The combined organic extracts were dried (sodium sulfate) and concentrated before being purified by flash chromatography eluting with 10% methanol in dichloromethane to give the title compound (300 mg) as a yellow oil that solidified on standing.

Compound 16a: 4-(1-(2-chlorophenoxy)ethyl)-6-(methylthio)-1,3,5-triazin-2-amine

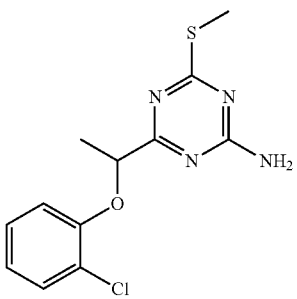 [SMILES: CSc1nc(N)nc(C(C)Oc2ccccc2Cl)n1]

To a solution of 1-(4-amino-6-(methylthio)-1,3,5-triazin-2-yl)ethanol (203 mg) in dry tetrahydrofuran (8 mL) was added 2-chlorophenol (0.122 mL) and triphenylphosphine (314 mg) followed by diisopropyl azodicarboxylate ((0.233 mL) dropwise. The solution was stirred at room temperature for 80 min then was concentrated in vacuo, dissolved in ethyl acetate (40 mL) and washed with 1N sodium hydroxide solution (2×40 mL), dried over sodium sulfate and concentrated to give a yellow oil. Purification by SCX chromatography eluting with a 1:1 mixture of dichloromethane-methanol then 2N ammonia in 1:1 mixture of dichloromethane-methanol followed by flash column chromatography, with 1% acetonirile in dichloromethane to give the title compound (207 mg).

In a similar manner was prepared:
16b: 4-(1-(2-chloro-4-fluorophenoxy)ethyl)-6-(methylthio)-1,3,5-triazin-2-amine starting from 2-chloro-4-fluorophenol.

Compound 17: 1-(4-amino-1,3,5-triazin-2-yl)ethanol

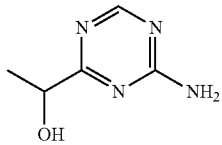

To a solution of 1-(4-amino-6-(methylthio)-1,3,5-triazin-2-yl)ethanol (398 mg) in ethanol (20 mL) was added Raney nickel 50% slurry in water (6 mL) and the reaction mixture was heated to 85° C. for 30 minutes then cooled to room temperature, filtered and evaporated to give the title compound (230 mg).

Compound 18a: (R)-2-bromo-6-(1-(2-chlorophenoxy)ethyl)pyridine

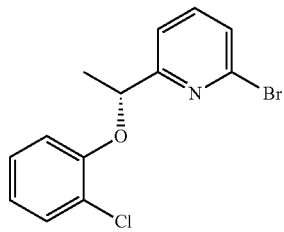 [SMILES: C[C@@H](Oc1ccccc1Cl)c1cccc(Br)n1]

A solution of (S)-1-(6-bromopyridin-2-yl)ethanol (1 g) (prepared by the method of S. Ishikawa, T. Hamada, K. Manabe, and S. Kobayashi, Synthesis 2005, 13, 2176-2182), 2-chlorophenol (0.615 mL, 0.764 g) and triphenylphosphine (1.558 g) in tetrahydrofuran (20 mL) under N2 and cooled to 0° C. A solution of diisopropyl azodicarboxylate (1.17 mL, 1.2 g) in tetrahydrofuran (10 mL) was then added dropwise and reaction warmed to room temperature overnight. The solvent was removed under reduced pressure, then heptane added to precipitate the triphenylphosphine oxide side product. Filtration and evaporation of the filtrate followed by purification by flash chromatography on silica eluting with heptane/ethyl acetate 8:2 gave the title compound (1.45 g) as a clear liquid.

In a similar manner were prepared the following compounds:
18b: (R)-2-bromo-6-(1-(2,4-difluorophenoxy)ethyl)pyridine starting from 2-chloro-4-fluorophenol.
18c: (R)-2-bromo-6-(1-(3-fluorophenoxy)ethyl)pyridine starting from 3-fluorophenol.

Compound 19: 1-(2-aminopyrimidin-4-yl)-2-(tert-butyldimethylsilyloxy)ethanol

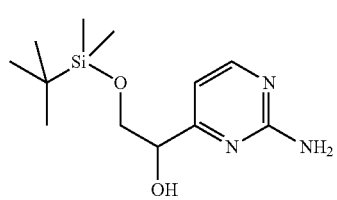 [SMILES: CC(C)(C)[Si](C)(C)OCC(O)c1ccnc(N)n1]

To a solution of 4-(2,2-dimethyl-1,3-dioxolan-4-yl)pyrimidin-2-amine (2f) (7.18 g) in methanol (300 mL) was added p-toluenesulfonic acid monohydrate (10.49 g) and the solution was stirred at room temperature overnight. The mixture was filtered through sodium carbonate and concentrated under vacuum to give a brown solid that was dissolved in N,N-dimethylformamide (400 mL) to which was added imidazole (5.2 g) and tert-butyldimethylsilyl chloride (7.7 g) and the solution was stirred at room temperature overnight. The mixture was concentrated on silica under vacuum and purified by silica flash chromatography eluting with 50% to 75% ethyl acetate in heptane to give the title compound (850 mg).

Compound 20a: 4-(2-(tert-butyldimethylsilyloxy)-1-(2-chloro-4-fluorophenoxy)ethyl)-pyrimidin-2-amine

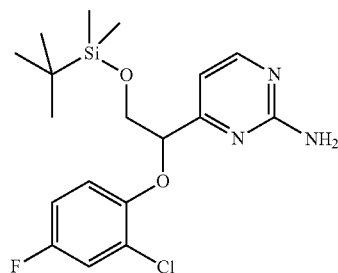 [SMILES: CC(C)(C)[Si](C)(C)OCC(Oc1ccc(F)cc1Cl)c1ccnc(N)n1]

To a solution of 1-(2-aminopyrimidin-4-yl)-2-(tert-butyldimethylsilyloxy)ethanol (19) (640 mg), 2-Chloro-4-fluorophenol (696 mg) and triphenylphosphine (1246 mg) in dichloromethane (10 mL) was added a solution of (E)-bis(4-chlorobenzyl) diazene-1,2-dicarboxylate in dichloromethane (20 mL) dropwise. The mixture was stirred at 45° C. overnight before being filtered and the filtrate was applied to a silica column and eluted with 10 to 100% ether in heptane. The product containing fractions were concentrated to afford the title compound (835 mg) as a white solid.

In a similar manner was prepared the following compound:
20b: 4-(2-(tert-butyldimethylsilyloxy)-1-(3-fluorophenoxy)ethyl)pyrimidin-2-amine starting from 3-fluorophenol.

Compound 21a: 2-(2-aminopyrimidin-4-yl)-2-(2-chloro-4-fluorophenoxy)ethanol

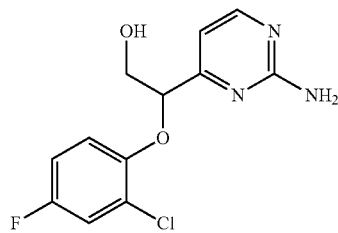 [SMILES: Nc1nccc(C(CO)Oc2ccc(F)cc2Cl)n1]

To a solution of 4-(2-(tert-butyldimethylsilyloxy)-1-(2-chloro-4-fluorophenoxy)ethyl)pyrimidin-2-amine (20a) (830 mg) in tetrahydrofuran (15 mL) was added tetrabutyl-ammonium fluoride (1 g) and the mixture was stirred at room temperature for 5 days. The mixture was concentrated and purified by column chromatography using 0 to 10% methanol in dichloromethane to give the title compound (348 mg) as a white solid.

In a similar manner was prepared the following compound:
21b: 2-(2-aminopyrimidin-4-yl)-2-(3-fluorophenoxy)ethanol starting from 4-(2-(tert-butyldimethylsilyloxy)-1-(3-fluorophenoxy)ethyl)pyrimidin-2-amine (20b).

EXAMPLES

Example 1A (R)-4-(1-(3-fluorophenoxy)ethyl)pyrimidin-2-amine

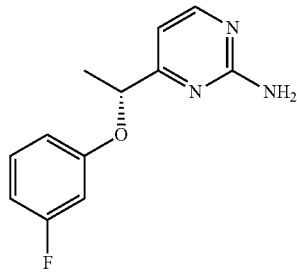 [SMILES: C[C@@H](Oc1cccc(F)c1)c1ccnc(N)n1]

(S)-1-(2-aminopyrimidin-4-yl)ethanol (6b) (7.75 g), 3-fluorophenol (6.87 g) and triphenylphosphine (16.07 g) were added to tetrahydrofuran (150 mL) under nitrogen and cooled to 0° C. (brine/ice bath). The resulting brown mixture was stirred at 0° C. for 20 min then diisopropyl azodicarboxylate (12.06 mL, 12.39 g) was added dropwise as a solution in tetrahydrofuran (40 mL). The reaction was maintained at 0-2° C. throughout the addition and was then allowed to warm to room temperature overnight. The solvent was removed under reduced pressure before the crude product was loaded onto a silica plug and purified by flash chromatography on silica eluting with heptane/ethyl acetate 7:3 followed by crystallisation from ethanol to give the title compound (6.2 g) as a white crystalline solid, MS (ES): m/z 234.0 [M+H]$^+$; $[\alpha]_D$–153.0 (methanol, c=1.8 mg/ml).

In a similar manner was prepared the following:
1B: (R)-4-(1-(2-chloro-5-fluorophenoxy)ethyl)pyrimidin-2-amine starting from 2-chloro-5-fluorophenol, MS (ES): m/z 268 [M+H]$^+$.
1C: (R)-4-(1-(2-chlorophenoxy)ethyl)pyrimidin-2-amine starting from 2-chlorophenol, MS (ES): m/z 250 [M+H]$^+$.
1D: (R)-4-(1-(2-trifluoromethylphenoxy)ethyl)pyrimidin-2-amine starting from 2-trifluoromethylphenol, MS (ES): m/z 284 [M+H]$^+$; $[\alpha]_D$–179.6 (methanol, c=0.9 mg/ml).
1E: (R)-4-(1-(2,5-difluorophenoxy)ethyl)pyrimidin-2-amine starting from 2,5-difluorophenol, MS (ES): m/z 252 [M+H]$^+$.
1F: (R)-4-(1-(2-chloro-4-fluorophenoxy)ethyl)pyrimidin-2-amine starting from 2-chloro-4-fluorophenol, MS (ES): m/z 268 [M+H]$^+$; $[\alpha]_D$–164.7 (methanol, c=2 mg/ml)
1G: (R)-4-(1-(3-bromophenoxy)ethyl)pyrimidin-2-amine starting from 3-bromophenol, MS (ES): m/z 295 [M+H]$^+$; $[\alpha]_D$–164.7 (methanol, c=2 mg/ml)
1H: (R)-4-(1-(2,5-dichlorophenoxy)ethyl)pyrimidin-2-amine starting from 2,5-dichlorophenol, MS (ES): m/z 284 [M]$^+$.
1I: (R)-4-(1-(2,4-difluorophenoxy)ethyl)pyrimidin-2-amine starting from 2,4-difluorophenol, MS (ES): m/z 252 [M+H]$^+$; $[\alpha]_D$–57.2 (methanol, c=3.7 mg/ml)
1J: (R)-4-(1-(2,3-difluorophenoxy)ethyl)pyrimidin-2-amine starting from 2,3-difluorophenol, MS (ES): m/z 252 [M+H]$^+$.
1K: (R)-4-(1-(3-fluoro-5-trifluoromethylphenoxy)ethyl)pyrimidin-2-amine starting from 3-fluoro-5-trifluoromethylphenol, MS (ES): m/z 302 [M+H]$^+$.
1L: (R)-4-(1-(2-chloro-5-trifluoromethylphenoxy)ethyl)pyrimidin-2-amine starting from 2-chloro-5-trifluoromethylphenol, MS (ES): m/z 318 [M+H]$^+$.
1M: (R)-4-(1-(3-methylphenoxy)ethyl)pyrimidin-2-amine starting from 3-methylphenol (m-cresol), MS (ES): m/z 230 [M+H]$^+$.
1N: (R)-4-(1-(2-chloro-5-methylphenoxy)ethyl)pyrimidin-2-amine starting from 2-chloro-5-methylphenol, MS (ES): m/z 264 [M+H]$^+$.
1O: (R)-4-(1-(2-chloro-4-trifluoromethylphenoxy)ethyl)pyrimidin-2-amine starting from 2-chloro-4-trifluoromethylphenol, MS (ES): m/z 318 [M+H]$^+$.
1P: (R)-4-(1-(3,4-dimethoxyphenoxy)ethyl)pyrimidin-2-amine starting from 3,4-dimethoxyphenol, MS (ES): m/z 276 [M+H]$^+$; $[\alpha]_D$–99.7 (methanol, c=1 mg/ml)
1Q: (R)-4-(1-(2-chloro-4-fluorophenoxy)ethyl)-N-methylpyrimidin-2-amine starting from (S)-1-(2-N-methylaminopyrimidin-4-yl)ethanol (6e) and 2-chloro-4-fluorophenol, MS (ES): m/z 282 [M+H]$^+$.
1R: (R)-4-(1-(3-fluorophenoxy)ethyl)-N-methylpyrimidin-2-amine starting from (S)-1-(2-N-methylaminopyrimidin-4-yl)ethanol (6e) and 3-fluorophenol, MS (ES): m/z 248 [M+H]$^+$.
1S: (R)-4-(1-(3-methoxypyridin-2-yloxy)ethyl)pyrimidin-2-amine starting from (S)-1-(2-aminopyrimidin-4-yl)ethanol (3) and 3-methoxy-2-(1H)-pyridone, MS (ES): m/z 247 [M+H]$^+$; $[\alpha]_D$–147.2 (methanol, c=1.6 mg/ml)
1T: (S)-4-(1-(3-fluorophenoxy)ethyl)pyrimidin-2-amine starting from 3-fluorophenol and (R)-1-(2-aminopyrimidin-4-yl)ethanol, MS (ES): m/z 234 [M+H]$^+$; $[\alpha]_D$+145.6 (methanol, c=1.33 mg/ml).
1U: (S)-4-(1-(2-trifluoromethylphenoxy)ethyl)pyrimidin-2-amine starting from 2-trifluoromethylphenol and (R)-1-(2-aminopyrimidin-4-yl)ethanol, MS (ES): m/z 284 [M+H]$^+$.
1V: (S)-4-(1-(2,5-difluorophenoxy)ethyl)pyrimidin-2-amine starting from 2,5-difluorophenol and (R)-1-(2-aminopyrimidin-4-yl)ethanol, MS (ES): m/z 268 [M+H]+.
1W: (S)-4-(1-(3-bromophenoxy)ethyl)pyrimidin-2-amine starting from 3-bromophenol and (R)-1-(2-aminopyrimidin-4-yl)ethanol, MS (ES): m/z 296 [M+H]$^+$; $[\alpha]_D$–132.3 (methanol, c=8.3 mg/ml)
1x: (R)-4-(1-(2-chloro-4-fluorophenoxy)propyl)pyrimidin-2-amine starting from (S)-1-(2-aminopyrimidin-4-yl)propanol (6d) and 2-chloro-4-fluorophenol, MS (ES): m/z 282 [M+H]$^+$; $[\alpha]_D$–128 (chloroform, c=0.5 mg/ml)
1Y: (R)-4-(1-(3-fluorophenoxy)propyl)pyrimidin-2-amine starting from (S)-1-(2-aminopyrimidin-4-yl)propanol (6d) and 3-fluorophenol, MS (ES): m/z 248 [M+H]$^+$; $[\alpha]_D$–104 (chloroform, c=0.5 mg/ml)
1Z: (S)-4-(1-(3-fluorophenoxy)propyl)pyrimidin-2-amine starting from (R)-1-(2-aminopyrimidin-4-yl)propanol (6c) and 3-fluorophenol, MS (ES): m/z 248 [M+H]$^+$; $[\alpha]_D$+99 (chloroform, c=0.5 mg/ml)

In a similar manner as described for Example 1a was prepared the following

Example 2A 4-(1-(3-trifluoromethylphenoxy)ethyl)pyrimidin-2-amine starting from 3-trifluoromethylphenol and 1-(2-aminopyrimidin-4-yl)ethanol, MS (ES): m/z 284 [M+H]$^+$ 2A: 4-(1-(3-chlorophenoxy)ethyl)pyrimidin-2-amine starting from 3-chlorophenol and 1-(2-aminopyrimidin-4-yl)ethanol, MS (ES): m/z 250 [M+H]$^+$.

2C: 4-(1-(3-trifluoromethoxyphenoxy)ethyl)pyrimidin-2-amine starting from 3-trifluoromethoxyphenol and 1-(2-aminopyrimidin-4-yl)ethanol, MS (ES): m/z 300 [M+H]$^+$.

2D: (R)-4-(1-(3-(trifluoromethyl)phenylthio)ethyl)pyrimidin-2-amine starting from (S)-1-(2-aminopyrimidin-4-yl)ethanol (6b) and 3-(trifluoromethyl)benzenethiol, MS (ES): m/z 298 [M−H]$^+$.

2E: (R)-4-(1-(2-chlorophenylthio)ethyl)pyrimidin-2-amine starting from (S)-1-(2-aminopyrimidin-4-yl)ethanol (Compound 6b) and 2-chlorobenzenethiol, MS (ES): m/z 266 [M+H]$^+$.

2F: (R)-4-(1-(3-fluorophenylthio)ethyl)pyrimidin-2-amine starting from (S)-1-(2-aminopyrimidin-4-yl)ethanol (6b) and 3-fluorobenzenethiol, MS (ES): m/z 250 [M+H]$^+$.

2G: (S)-4-(1-(2-chloro-4-fluorophenoxy)propyl)pyrimidin-2-amine starting from (R)-1-(2-aminopyrimidin-4-yl)propanol (6c) and 2-chloro-4-fluorophenol, MS (ES): m/z 282 [M+H]$^+$; $[\alpha]_D$+128.9 (chloroform, c=0.5 mg/ml)

2H: 4-(1-(2-chloro-4-fluorophenoxy)ethyl)pyrimidin-2-amine starting from 1-(2-aminopyridin-4-yl)ethanol (14a) and 2-chloro-4-fluorophenol, MS (ES): m/z 267 [M+H]$^+$.

2I: 4-(1-(2-chloro-4-fluorophenoxy)ethyl)-1,3,5-triazin-2-amine starting from 1-(4-amino-1,3,5-triazin-2-yl)ethanol (18) and 2-chloro-4-fluorophenol, MS (ES): m/z 269 [M+H]$^+$.

2J: (R)-4-(1-(2-chloro-4-fluorophenoxy)ethyl)-2-(pyrrolidin-1-yl)pyrimidine starting from (R)-1-(2-(pyrrolidin-1-yl)pyrimidin-4-yl)ethanol (6f) and 2-chloro-4-fluorophenol, MS (ES): m/z 322 [M+H]$^+$.

2K: (4-(1-(3-(trifluoromethyl)pyridin-2-ylthio)ethyl)pyrimidin-2-amine starting from 1-(2-aminopyrimidin-4-yl)ethanol (5a) and 3-(trifluoromethyl)pyridine-2-thiol, MS (ES): m/z 301 [M+H]$^+$.

Example 3A (R)-4-(1-(3-(trifluoromethyl)pyridin-2-yloxy)ethyl)pyrimidin-2-amine

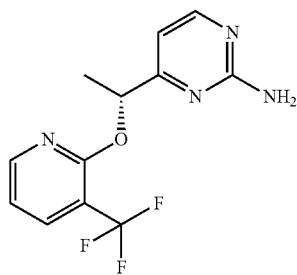 [SMILES: C[C@@H](Oc1ncccc1C(F)(F)F)c1ccnc(N)n1]

To a solution of (R)-1-(2-aminopyrimidin-4-yl)ethanol (6a) (250 mg) in dry N-methylmorpholine (4 mL) at ambient temperature was added potassium 2-methylpropan-2-olate (222 mg) and the solution was left to stir for 30 min then 2-fluoro-3-(trifluoromethyl)pyridine (282 mg) was added the mixture was stirred for 10 min at ambient temperature and then heated to 100° C. with microwave irradiation for 2 minutes then cooled and quenched into water (50 mL). The precipitated solid was filtered and washed with water and air dried under a slight vacuum. The semi-dried material was taken up in methylene chloride and dried over magnesium sulfate to which activated charcoal was added then filtered through a bed of dicalite and evaporated to give the title compound (359 mg), MS (ES): m/z 285 [M+H]$^+$.

In a similar manner were prepared the following compounds:

3B: 4-(1-(3-methoxypyridin-2-yloxy)ethyl)pyrimidin-2-amine starting from 1-(2-aminopyrimidin-4-yl)ethanol (5a) and 2-chloro-3-methoxypyridine, MS (ES): m/z 247 [M+H]$^+$.

3C: 4-(1-(3-(trifluoromethyl)pyridin-2-yloxy)ethyl)pyrimidin-2-amine starting from 1-(2-aminopyridin-4-yl)ethanol (14a) and 2-chloro-3-(trifluoromethyl)pyridine, MS (ES): m/z 284 [M+H]$^+$.

3D: 4-(1-(4-(trifluoromethyl)pyrimidin-2-yloxy)ethyl)pyridin-2-amine starting from 1-(2-aminopyridin-4-yl)ethanol (14a) and 2-chloro-4-(trifluoromethyl)pyrimidine, MS (ES): m/z 285 [M+H]$^+$.

Example 4A (R)-4-(1-(3-methoxypyrazin-2-yloxy)ethyl)pyrimidin-2-amine

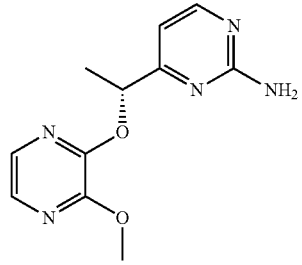 [SMILES: COc1nccnc1O[C@H](C)c1ccnc(N)n1]

To a solution of (R)-1-(2-aminopyrimidin-4-yl)ethanol (6a) (1 g) in dry N-methylmorpholine (15 mL) was added sodium hydride (0.302 g, 60% dispersion in oil) maintaining a reaction temperature below 25° C. using a water bath. Once the addition was complete the cooling bath was removed and mixture left to stir for 30 minutes then a solution of 2-chloro-3-methoxypyrazine (1.039 g) in dry N-methylmorpholine (2 mL) was added and the reaction mixture was left to stir overnight at ambient temperature. The mixture was quenched into water (300 mL) and extracted with ethyl acetate (4×100 mL) and the combined organics was washed with a 10% w/v solution lithium chloride solution (2×100 mL) then with saturated brine, dried over magnesium sulfate, filtered and evaporated to give a pale brown solid. Purification on a 100 g silica column eluting with 100% ethyl acetate followed by crystallisation from ethyl acetate gave the title product (520 mg), MS (ES): m/z 248 [M+H]$^+$; $[\alpha]_D$−110.9 (methanol, c=2 mg/ml)

In a similar manner were prepared the following compounds:

4B: 4-(2,2,2-trifluoro-1-(3-(trifluoromethyl)pyridin-2-yloxy)ethyl)pyrimidin-2-amine starting from 1-[2-aminopyrimidin-4-yl]-2,2,2-trifluoroethanol (10a) and 2-fluoro-3-(trifluoromethyl)pyridine, MS (ES): m/z 339 [M+H]$^+$.

4C: (R)-4-(1-(3-(trifluoromethyl)pyridin-2-yloxy)propyl)pyrimidin-2-amine starting from (R)-1-(2-aminopyrimidin-4-yl)propanol (6c) and 2-fluoro-3-(trifluoromethyl)pyridine, MS (ES): m/z 299 [M+H]$^+$; $[\alpha]_D$−122.4 (chloroform, c=0.5 mg/ml).

4D: 4-(1-(3-(trifluoromethyl)pyridin-2-yloxy))ethyl)-N-methylpyrimidin-2-amine starting from 1-[2-(N-methylamino)pyrimidin-4-yl]ethanol (5c) and 2-fluoro-3-(trifluoromethyl)pyridine, MS (ES): m/z 299 [M+H]$^+$.

4E: 4-(1-(6-methyl-pyridin-2-yloxy))ethyl)-N-methylpyrimidin-2-amine starting from 1-[2-(N-methylamino)pyrimidin-4-yl]ethanol (5c) and 2-fluoro-6-methyl-pyridine, MS (ES): m/z 245 [M+H]$^+$.

4F: 4-(1-(3-bromo-5-methyl-pyridin-2-yloxy))ethyl)-N-methylpyrimidin-2-amine starting from 1-[2-(N-methylamino)pyrimidin-4-yl]ethanol (5c) and 2-chloro-3-bromo-5-methylpyridine, MS (ES): m/z 324 [M+H]$^+$.

4G: 4-(1-(6-(trifluoromethyl)pyridin-2-yloxy)ethyl)pyrimidin-2-amine starting from 1-(2-aminopyrimidin-4-yl)ethanol (5a) and 2-fluoro-6-(trifluoromethyl)pyridine, MS (ES): m/z 285 [M+H]$^+$.

4H: 4-(1-(3-chloropyridin-2-yloxy)ethyl)pyrimidin-2-amine starting from 1-(2-aminopyrimidin-4-yl)ethanol (5a) and 2,3-dichloropyridine, MS (ES): m/z 251 [M+H]$^+$.

4I: (S)-4-(1-(3-(trifluoromethyl)pyridin-2-yloxy)propyl)pyrimidin-2-amine starting from (S)-1-(2-aminopyrimidin-4-yl)propanol (6b) and 2-chloro-3-(trifluoromethyl)pyridine, MS (ES): m/z 299 [M+H]$^+$; $[\alpha]_D$–122.4 (chloroform, c=0.5 mg/ml).

4J: 4-(1-(6-(trifluoromethyl)pyrazin-2-yloxy)ethyl)pyrimidin-2-amine starting from 1-(2-aminopyrimidin-4-yl)ethanol (5a) and 2-chloro-6-(trifluoromethyl)pyrazine (prepared from 3-(trifluoromethyl)pyrazine 1-oxide as described in *J. Med. Chem.* 1978, 21, 536), MS (ES): m/z 286 [M+H]$^+$.

4K: (R)-4-(1-(6-(trifluoromethyl)pyridin-2-yloxy)ethyl)pyrimidin-2-amine starting from (R)-1-(2-aminopyrimidin-4-yl)ethanol (5a) and 2-fluoro-6-(trifluoromethyl)pyridine, MS (ES): m/z 285 [M+H]$^+$.

4L: 4-(1-(6-bromo-4-methylpyridin-2-yloxy)ethyl)pyrimidin-2-amine starting from 1-(2-aminopyrimidin-4-yl)ethanol (5a) and 3-bromo-2-chloro-5-methylpyridine, MS (ES): m/z 309 [M]$^+$.

4M: 4-(1-(6-bromopyridin-2-yloxy)ethyl)pyrimidin-2-amine starting from 1-(2-aminopyrimidin-4-yl)ethanol (5a) and 2-bromo-6-fluoropyridine, MS (ES): m/z 297 [M+H]$^+$.

4N: (R)-4-(1-(6-fluoro-pyridin-2-yloxy)ethyl)pyrimidin-2-amine starting from (R)-1-(2-aminopyrimidin-4-yl)ethanol (5a) and 2,3-difluoro-pyridine, MS (ES): m/z 235 [M+H]$^+$.

4O: 4-(1-(6-methylpyridin-2-yloxy)ethyl)pyrimidin-2-amine starting from 1-(2-aminopyrimidin-4-yl)ethanol (5a) and 2-fluoro-6-methylpyridine, MS (ES): m/z 231 [M+H]$^+$.

4P: (R)-4-(1-(4-(trifluoromethyl)pyrimidin-2-yloxy)ethyl)pyrimidin-2-amine starting from (R)-1-(2-aminopyrimidin-4-yl)ethanol (5a) and 2-chloro-4-(trifluoromethyl)pyrimidine, MS (ES): m/z 286 [M+H]$^+$; $[\alpha]_D$–53.9 (methanol, c=1.7 mg/ml).

4Q: (R)-4-(1-(pyridin-2-yloxy)ethyl)pyrimidin-2-amine starting from (R)-1-(2-aminopyrimidin-4-yl)ethanol (5a) and 2-fluoropyridine, MS (ES): m/z 217 [M+H]$^+$; $[\alpha]_D$–92.1 (methanol, c=2.5 mg/ml).

Example 5A 4-(1-(3-(trifluoromethyl)pyridin-2-ylamino)ethyl)pyrimidin-2-amine

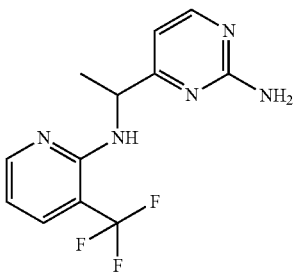 [SMILES: CC(Nc1ncccc1C(F)(F)F)c1ccnc(N)n1]

To a solution of 2-chloro-3-(trifluoromethyl)pyridine (526 mg), 1-(2-aminopyrimidin-4-yl)-ethylamine (12a) (400 mg), 2,2'-bis(diphenylphosphino)-1,1'-binaphthyl (BINAP; 108 mg) and sodium tert-butoxide (334 mg) in dry nitrogen flushed toluene (40 mL) and flushed with argon. Palladium (II) acetate (26 mg) was added and the reaction mixture was heated to 70° C. overnight under an argon atmosphere. The reaction mixture was poured on water (200 mL) and extracted with ethylacetate (3×200 mL). The combined organic extracts were washed with brine (400 mL), dried over sodium sulfate and concentrated in vacuo to afford material that was purified by column chromatography (40% ethylacetate in heptane to 80% ethylacetate in heptane). Fractions containing product were concentrated in vacuo and purified by column chromatography to afford 241 mg of the title compound as a clear orange oil, MS (ES): m/z 284 [M+H]$^+$.

In a similar manner was prepared the following compound:

5B: 4-(1-(4-(trifluoromethyl)pyrimidin-2-ylamino)ethyl)pyrimidin-2-amine starting from 2-chloro-4-(trifluoromethyl)pyrimidine, MS (ES): m/z 285 [M+H]$^+$.

Example 6

4-(1-(3-(methylthio)pyridin-2-yloxy)ethyl)pyrimidin-2-amine

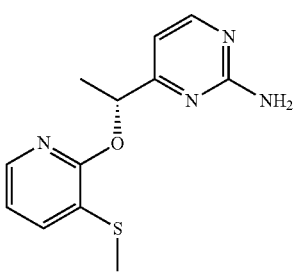 [SMILES: CSc1cccnc1O[C@H](C)c1ccnc(N)n1]

To a solution of (R)-4-(1-(6-fluoro-pyridin-2-yloxy)ethyl) pyrimidin-2-amine (389 mg) (prepared as described for (R)-4-(1-(6-fluoro-pyridin-2-yloxy)ethyl)pyrimidin-2-amine but starting from 1-(2-aminopyrimidin-4-yl)ethanol) in dry dimethylsulfoxide (10 mL) was added sodium methanethiolate (582 mg) the solution was stirred for 5 min and then heated with microwave irradiation at 140° C. for 300 sec. The resulting mixture was quenched into water (300 mL) the resulting solid was filtered and washed with water and dried. The solid was triturated with heptane and further to give the title compound (226 mg) as a pale brown solid, MS (ES): m/z 263 [M+H]+.

Example 7A (R)-6-(1-(2-chlorophenoxy)ethyl)pyridin-2-amine

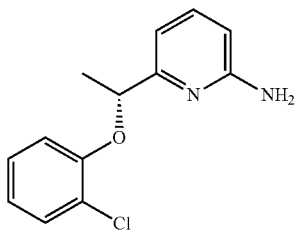 [SMILES: C[C@@H](Oc1ccccc1Cl)c1cccc(N)n1]

(R)-(+)-2,2'-Bis(diphenylphosphino)-1,1'-binaphthyl (30 mg), palladium (II) acetate (7.2 mg) and cesium carbonate (0.365 g) were added to a 3-neck flask fitted with thermometer, a condenser and a nitrogen inlet. System was purged with nitrogen then a solution of (R)-2-bromo-6-(1-(2-chlorophenoxy)ethyl)pyridine (18a) (0.25 g) and benzophenone imine (0.174 g) in toluene (40 mL) was added and reaction stirred at room temperature for 30 min. Reaction was then heated at 95° C. for 20 h, cooled, diluted with ether and filtered through dicalite. The filter cake was washed with ether and the filtrate concentrated under reduced pressure to give an orange gum that was purified by column chromatography on silica eluting with heptane/ethyl acetate (7:3) to give a yellow gum that was taken up in tetrahydrofuran (5 mL) and then 2M HCl (3 ml) was added and reaction left overnight at room temperature. Subjecting the mixture to purification by column chromatography on silica eluting with heptane/ethyl acetate (7:3) gave the title product (88 mg) a pale yellow gum, MS (ES): m/z 249 [M+H]+.

In a similar manner were prepared the following compounds:

7B: (R)-6-(1-(2,4-difluorophenoxy)ethyl)pyridin-2-amine starting from (R)-2-bromo-6-(1-(2,4-difluorophenoxy)ethyl)pyridine (18b), MS (ES): m/z 251 [M+H]+.

7C: (R)-6-(1-(3-fluorophenoxy)ethyl)-N,N-dimethylpyridin-2-amine starting from (R)-2-bromo-6-(1-(3-fluorophenoxy)ethyl)pyridine (18c) and dimethylamine, omitting the acidic deprotection step, MS (ES): m/z 261 [M+H]+.

7D: (R)-2-(1-(3-fluorophenoxy)ethyl)-6-(pyrrolidin-1-yl)pyridine starting from (R)-2-bromo-6-(1-(3-fluorophenoxy)ethyl)pyridine (18c) and pyrrolidine, omitting the acidic deprotection step, MS (ES): m/z 287 [M+H]+.

7E: (R)-2-(azetidin-1-yl)-6-(1-(3-fluorophenoxy)ethyl)pyridine starting from (R)-2-bromo-6-(1-(3-fluorophenoxy)

ethyl)pyridine (18c) and azetidine, omitting the acidic deprotection step, MS (ES): m/z 273 [M+H]+.

Example 8

4-(1-(2-chlorophenoxy)ethyl)-1,3,5-triazin-2-amine

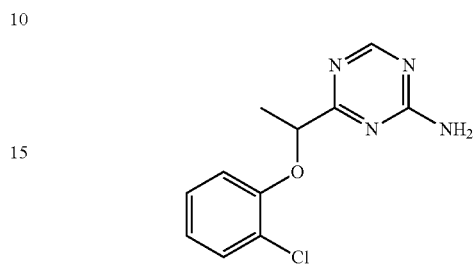

To a solution of 4-(1-(2-chlorophenoxy)ethyl)-6-(methylthio)-1,3,5-triazin-2-amine (16a) (181 mg) in ethanol (10 mL) was added. Raney-nickel was added via a syringe (2.0 mL) and the reaction mixture was heated at 85° C. for 40 minutes then cooled to room temperature and the mixture was filtered over Celite and washed with ethanol/water (1/1 v/v) and methanol. The filtrate was concentrated in vacuo and further purified by column chromatography (eluting with 1% acetontrile in dichloromethane) to give the title compound (25 mg), MS (ES): m/z 251 [M+H]+.

Example 9A 4-(1-(2-chloro-4-fluorophenoxy)-2-methoxyethyl)pyrimidin-2-amine

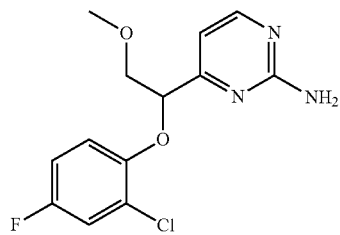 [SMILES: COCC(Oc1ccc(F)cc1Cl)c1ccnc(N)n1]

To a solution of 2-(2-aminopyrimidin-4-yl)-2-(2-chloro-4-fluorophenoxy)ethanol (21a) (185 mg) in dry tetrahydrofuran under nitrogen atmosphere was added sodium hydride (23 mg, 60% dispersion in oil) and the mixture was stirred at room temperature for 10 minutes, then methyl iodide (0.045 mL) was added. The mixture was stirred at room temperature for an additional for 45 minutes, poured onto sat aq ammonium chloride solution then extracted with ethyl acetate, washed with brine, dried over sodium sulfate and in vacuo. Purification by column chromatography eluting with 10 to 100% ether in heptane afforded the title compound (60 mg) as an oil that solidified upon standing, MS (ES): m/z 298 [M+H]+.

In a similar manner was prepared the following compound:

9B: 4-(1-(3-fluorophenoxy)-2-methoxyethyl)pyrimidin-2-amine starting from 2-(2-aminopyrimidin-4-yl)-2-(3-fluorophenoxy)ethanol (2), MS (ES): m/z 264 [M+H]+.

Example 10

Biological Testing Using Automated Patch Clamp Electrophysiology

A: Cell Culture

HEK-hHCN1-2H10 cells were cultured in 225 cm² flasks, in MEM (with Earle's salts) supplemented with 10% Fetalclone II+0.1 mM non essential amino acids+1 mM sodium pyruvate+10 mM HEPES+0.5 mg/mL G418. The cells were routinely maintained at 37° C. in an atmosphere of 5% $CO_2$ and 100% relative humidity until 50% confluent. 24 hours before use, cells were incubated at 30° C. to increase HCN1 membrane expression and harvested immediately prior to patch clamp experiments. The growth medium was aspirated under vacuum and the cells are washed in 50 mL Dulbecco's Phosphate Buffered Saline (without $CaCl_2$ and $MgCl_2$; D-PBS). The cells are then dissociated by incubating with 5 mL of a 1:1 mixture of 0.1% Trypsin/0.04% EDTA and cell dissociation buffer (CDS), at 37° C. for 2 minutes. Cell dissociation was terminated by the addition of 5 mL growth medium after which, the cells were mechanically dissociated by gently triturating 3-4 times using a 10 mL pipette. The cells were counted using a haemocytometer, recovered by centrifugation at 212 g for 1½ minutes and resuspended in 5 mLs of filtered external recording solution (see below). The cells were re-covered again by centrifugation as above and resuspended in filtered extracellular solution at a density of $2 \times 10^6$ cells per mL, triturating 4-5 times. The cells were transferred immediately to IonWorks.

B: Patch Clamp Recordings

Automated patch clamp recordings were performed using the IonWorks Quattro (MDS Analytical Technologies). The IonWorks Quattro was primed with intracellular (in mM: KGluconate, 130; NaCl, 10; $MgCl_2$, 1; EGTA, 1; HEPES, 10, pH 7.35) and extracellular solution (in mM: NaGluconate, 104; NaCl, 10; KCl, 30; $MgCl_2$, 1; $CaCl_2$, 1.8; Hepes, 10; glucose, 5; pH 7.35) recording solutions. Perforated patch clamp recordings were established with 0.1 mg/mL amphotericin B (in 0.36% DMSO) and the cells voltage clamped at −40 mV. Whole cell perforated patch clamp recordings were performed in two separate runs, with voltage steps to −80 mV and −120 mV for 1 s; leak subtraction was performed using a −10 mV voltage pulse prior to channel activation. Compounds were tested at 12 concentrations (half log intervals; 1% DMSO) and incubated for 10 minutes between current recordings. Cells were excluded with whole cell currents less 100 pS, seal resistances<50MΩ or if the seal resistance varied by >50% during the course of the experiment. The amplitude of the time-dependent currents mediated by HCN, both pre- and post compound addition, was measured as the difference between the current recorded immediately after the capacity transient on stepping to the test voltage and the current measured after it had reached a steady state amplitude. Data were processed using the IonWorks Quattro System Software version 2 and analysed in Activity Base with XLFit 4.1, using a standard 4 parameter logistic function. Concentration response curves were generated and compound potency at the hHCN1 channel reported as the $pEC_{50}$, with the appropriate confidence intervals.

Compounds of the invention block the Ih current by >50% at 300 µM; a preferred set of the compounds have a $pEC_{50}$ activity of greater than 4 at the −80 mV voltage step and further preferred compounds of the invention have a $pEC_{50}$ activity greater than 5 at the −80 mV voltage step.

Example 11

The Rat (Chung) Model of Neuropathic Pain

In this model, mechanical allodynia is induced by tight ligation of the left L5 spinal nerve. This assay has been employed successfully to demonstrate anti-allodynic effects of anticonvulsants (gabapentin), antidepressants (duloxetine) and opioid analgesics (morphine) which are used clinically in the treatment of neuropathic pain. Male Wistar rats (228-301 g body weight at time of surgery) were employed in the study. Rats were placed on an elevated (~40 cm) mesh floor in perspex boxes and the rats' withdrawal threshold to a mechanical stimulus (calibrated von Frey filaments) was measured using filaments of increasing force (2.6-167 mN). The von Frey filaments were applied to the plantar surface of the paw and threshold response determined using the up and down method (Chaplan S. R. et al., J. Neurosci. Methods 53: 55-63, 1994; Dixon. J. Ann. Rev. Pharmacol. toxicol. 20: 441-462, 1980). A positive response was noted if the paw was sharply withdrawn. A cut-off of 15 g was selected as the upper limit for testing. Following baseline measurements each animal was anaesthetised and the L5 spinal nerve tightly ligated. The animals were allowed to recover from the surgery for a period of at least three days. On the day of drug administration the paw withdrawal thresholds were re-measured (0 min). Immediately after this reading, the rats were dosed orally with vehicle or test compound and readings measured at various time points after compound administration.

Data were expressed as mean±s.e.m. Statistical analysis was performed using the Kruskal-Wallis one-way analysis of variance, a non-parametric statistical test. Each of the treatment groups were then compared against the vehicle group, using the non-parametric Dunn's test. The $ED_{50}$ (dose at which allodynia is reversed by approximately 50%) value was also calculated at $t_{max}$ using linear regression (sigmoidal dose response; variable slope) with constants of 0 and 15 g (cut-off) for the bottom and top, respectively (XLFit software).

The invention claimed is:

1. An amino-heteroaryl derivative according to general Formula 1:

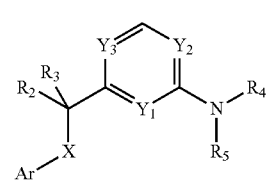

Formula 1 wherein
Ar represents a 6-membered heteroaryl group containing 1 or 2 nitrogen atoms, which can be optionally substituted with one or more substituents selected from halogen, $(C_{1-4})$alkyl, halo$(C_{1-4})$alkyl, $(C_{1-4})$alkyloxy, halo$(C_{1-4})$ alkyloxy, CN, $(C_{1-4})$alkylthio and halo$(C_{1-4})$alkylthio;
X is O, S, or $NR_1$;
$R_1$ is H or $(C_{1-4})$alkyl;
$R_2$ is $(C_{1-4})$alkyl, halo$(C_{1-4})$alkyl, $(C_{1-4})$alkyloxy$(C_{1-4})$ alkyl or
halo$(C_{1-4})$alkyloxy$(C_{1-4})$alkyl;
$R_3$ is H, $(C_{1-4})$alkyl, halo$(C_{1-4})$alkyl, $(C_{1-4})$alkyloxy $(C_{1-4})$alkyl or halo$(C_{1-4})$alkyloxy$(C_{1-4})$alkyl; or R$_2$ and R$_3$ form together with the carbon atom to which they are bonded a 3-7 membered saturated ring optionally containing an oxygen atom;

Y$_1$, and Y$_2$ are N; and Y$_3$ is =(CH)—;

R$_4$ and R$_5$ are independently H, (C$_{1-4}$)alkyl, halo(C$_{1-4}$)alkyl or (C$_{1-4}$)alkyloxy(C$_{1-4}$)alkyl; or R$_4$ and R$_5$ form together with the nitrogen atom to which they are bonded a 3-7 membered saturated ring optionally containing an oxygen atom; or a pharmaceutically acceptable salt thereof.

2. An amino-heteroaryl derivative of claim 1 or a pharmaceutically acceptable salt thereof, wherein Ar represents substituted pyridin-2-yl, pyridin-3-yl, pyridin-4-yl, pyrazin-2-yl or pyrimidin-2-yl.

3. The amino-heteroaryl derivative of claim 2 or a pharmaceutically acceptable salt thereof, wherein R$_2$ is CH$_3$ and R$_3$ is H.

4. The amino-heteroaryl derivative of claim 3 or a pharmaceutically acceptable salt thereof, wherein R$_4$ and R$_5$ are H.

5. An amino-heteroaryl derivative which is:
(R)-4-(1-(3-fluorophenoxy)ethyl)pyrimidin-2-amine;
(R)-4-(1-(2-chloro-5-fluorophenoxy)ethyl)pyrimidin-2-amine;
(R)-4-(1-(2,5-difluorophenoxy)ethyl)pyrimidin-2-amine;
(R)-4-(1-(2,4-difluorophenoxy)ethyl)pyrimidin-2-amine;
(R)-4-(1-(3-methoxypyridin-2-yloxy)ethyl)pyrimidin-2-amine;
(S)-4-(1-(3-fluorophenoxy)ethyl)pyrimidin-2-amine;
(S)-4-(1-(2,5-difluorophenoxy)ethyl)pyrimidin-2-amine;
4-(1-(3-(trifluoromethyl)pyridin-2-ylthio)ethyl)pyrimidin-2-amine;
(R)-4-(1-(3-(trifluoromethyl)pyridin-2-yloxy)ethyl)pyrimidin-2-amine;
(R)-4-(1-(4-(trifluoromethyl)pyrimidin-2-yloxy)ethyl)pyrimidin-2-amine; and
4-(1-(3-(trifluoromethyl)pyridin-2-ylamino)ethyl)pyrimidin-2-amine;

or a pharmaceutically acceptable salt thereof.

6. The amino-heteroaryl derivative of claim 5 which is selected from:
(R)-4-(1-(3-methoxypyridin-2-yloxy)ethyl)pyrimidin-2-amine;
(4-(1-(3-(trifluoromethyl)pyridin-2-ylthio)ethyl)pyrimidin-2-amine;
(R)-4-(1-(3-(trifluoromethyl)pyridin-2-yloxy)ethyl)pyrimidin-2-amine;
(R)-4-(1-(4-(trifluoromethyl)pyrimidin-2-yloxy)ethyl)pyrimidin-2-amine; and
4-(1-(3-(trifluoromethyl)pyridin-2-ylamino)ethyl)pyrimidin-2-amine;

or a pharmaceutically acceptable salt thereof.

7. A pharmaceutical composition comprising an amino-heteroaryl derivative of claim 1 or a pharmaceutically acceptable salt thereof in admixture with pharmaceutically acceptable auxiliaries.

8. A method of specifically inhibiting the I$_h$ HCN channel comprising administering to a patient in which the I$_h$ HCN channel is to be inhibited a therapeutically effective amount of a compound of claim 1 or a pharmaceutically acceptable salt thereof.

9. The method according to claim 8, wherein the patient is experiencing neuropathic pain arising from Ih HCN channel activity.

10. The method according to claim 8, wherein the patient is experiencing inflammatory pain arising from Ih HCN channel activity.

* * * * *